(12) United States Patent
Yeh et al.

(10) Patent No.: US 9,274,131 B2
(45) Date of Patent: Mar. 1, 2016

(54) DROPLET MANIPULATING DEVICE AND METHOD FOR MANIPULATING DROPLET

(71) Applicant: INDUSTRIAL TECHNOLOGY RESEARCH INSTITUTE, Hsinchu (TW)

(72) Inventors: Shao-Hsing Yeh, Hsinchu (TW); Yu-Ying Lin, Tainan (TW); Chi-Han Chiou, Tainan (TW); Liang-Ju Chien, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/293,661

(22) Filed: Jun. 2, 2014

(65) Prior Publication Data

US 2015/0027554 A1      Jan. 29, 2015

(30) Foreign Application Priority Data

Jul. 26, 2013   (TW) .............................. 102126955 A

(51) Int. Cl.
*G01N 15/06*    (2006.01)
*G01N 33/00*    (2006.01)
(Continued)

(52) U.S. Cl.
CPC ...... *G01N 35/0098* (2013.01); *B01L 3/502784* (2013.01); *B03C 1/01* (2013.01); *B03C 1/035* (2013.01); *B03C 1/0335* (2013.01); *B03C 1/288* (2013.01); *B01L 3/502761* (2013.01); *B01L 2200/0647* (2013.01); *B01L 2300/087* (2013.01); *B01L 2400/043* (2013.01);
(Continued)

(58) Field of Classification Search
CPC ........ G01N 15/06; G01N 33/00; G01N 33/48
USPC ............ 422/68.1, 502, 503, 504; 436/43, 180
See application file for complete search history.

(56) References Cited

U.S. PATENT DOCUMENTS 5,541,072 A * 7/1996 Wang et al. .................. 435/7.21
6,013,188 A * 1/2000 Terstappen et al. ........... 210/695
(Continued)

FOREIGN PATENT DOCUMENTS

CN    101087655 A    12/2007
CN    101375166 A    2/2009
(Continued)

OTHER PUBLICATIONS

M. Shikida et al., Magnetic handling of droplet in micro chemical analysis system utilizing surface tension and wettability, IEEE, 2004, p. 359-362.
(Continued)

*Primary Examiner* — Brian J Sines
(74) *Attorney, Agent, or Firm* — Locke Lord LLP; Tim Tingkang Xia, Esq.

(57) ABSTRACT

The disclosure relates to a droplet manipulating device and a method for manipulating a droplet. The droplets manipulating device includes a first magnetic field generator, a second magnetic field generator, and a flow channel. The first magnetic field generator produces a first magnetic field on the droplet, so that the droplet has the direction of magnetic field corresponding to the first magnetic field. Further, the second magnetic field generator produces a second magnetic field on the droplet so as to drive the droplet to be in motion in the flow channel.

11 Claims, 40 Drawing Sheets

(51) Int. Cl.
*G01N 33/48* (2006.01)
*G01N 35/00* (2006.01)
*B03C 1/01* (2006.01)
*B03C 1/033* (2006.01)
*B03C 1/035* (2006.01)
*B03C 1/28* (2006.01)
*B01L 3/00* (2006.01)

(52) U.S. Cl.
CPC ........ *B03C 2201/18* (2013.01); *B03C 2201/26* (2013.01); *Y10T 137/0391* (2015.04); *Y10T 137/206* (2015.04)

(56) References Cited

U.S. PATENT DOCUMENTS

| | | | |
|---|---|---|---|
| 7,309,439 | B2 | 12/2007 | Fernandez et al. |
| 7,820,454 | B2 | 10/2010 | Su et al. |
| 7,935,906 | B2 | 5/2011 | Kibar et al. |
| 8,051,878 | B2 | 11/2011 | Delamarche |
| 8,067,176 | B2 | 11/2011 | Ohashi |
| 8,084,270 | B2 | 12/2011 | Prins et al. |
| 8,093,064 | B2 | 1/2012 | Shah et al. |
| 8,216,855 | B2 | 7/2012 | Pipper et al. |
| 8,932,540 | B2 * | 1/2015 | Den Toonder et al. ....... 422/500 |
| 2005/0170418 | A1 | 8/2005 | Moreland et al. |
| 2006/0037657 | A1 | 2/2006 | Shibata et al. |
| 2008/0226500 | A1 | 9/2008 | Shikida et al. |
| 2010/0233822 | A1 | 9/2010 | Prins et al. |
| 2011/0104747 | A1 | 5/2011 | Pollack et al. |
| 2012/0135533 | A1 | 5/2012 | Shikida et al. |

FOREIGN PATENT DOCUMENTS

| | | |
|---|---|---|
| CN | 101438142 A | 5/2009 |
| CN | 102481575 A | 5/2012 |
| CN | 102586226 A | 7/2012 |
| TW | 200506365 A | 2/2005 |
| TW | I319434 A | 1/2010 |
| TW | 201022676 A | 6/2010 |
| TW | I329165 B | 8/2010 |
| TW | 201040526 A | 11/2010 |
| WO | 0231505 A1 | 4/2002 |

OTHER PUBLICATIONS

Qasem Ramadan et al., Fabrication of Three-Dimensional Magnetic Microdevices With Embedded Microcoils for Magnetic Potential Concentration, Journal of Microelectromechanical Systems, 2006, p. 624-638, vol. 15, No. 3.

Nam-Trung Nguyen et al., Kinematics and deformation of ferrofluid droplets under magnetic actuation, Microfluid Nanofluid, 2007, p. 571-579, 3.

Qasem Ramadan et al., Microcoils for transport of magnetic beads, Applied Physics Letters, 2006, 032501, 88.

Ali Beyzavi et al., Programmable two-dimensional actuation of ferrofluid droplet using planar microcoils, Journal of Micromechanics and Microengineering, 2010, 015018, 20.

State Intellectual Property Office of the P. R. C, "Office Action", Oct. 28, 2015, China.

* cited by examiner

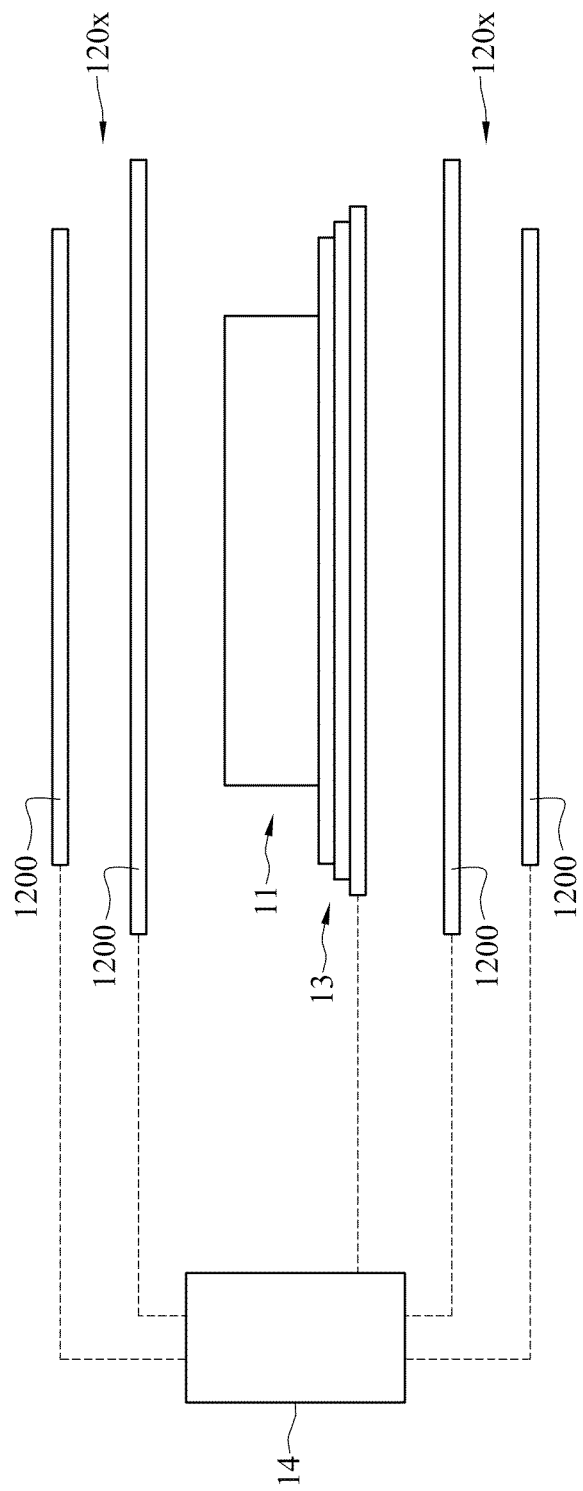

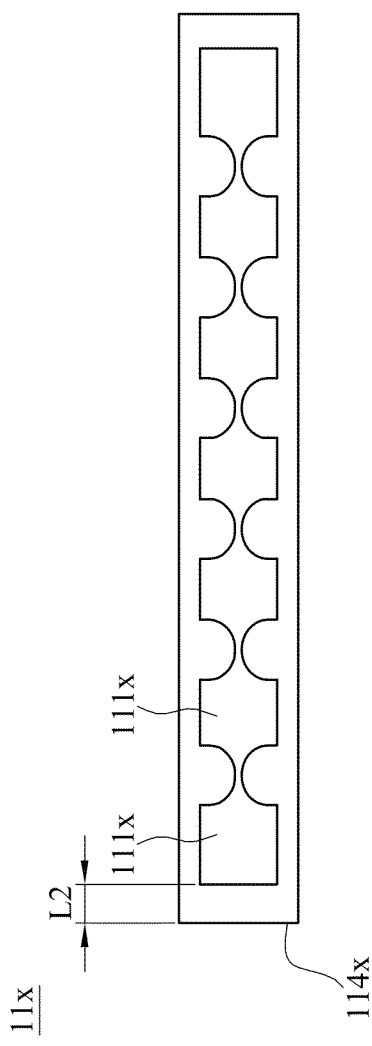
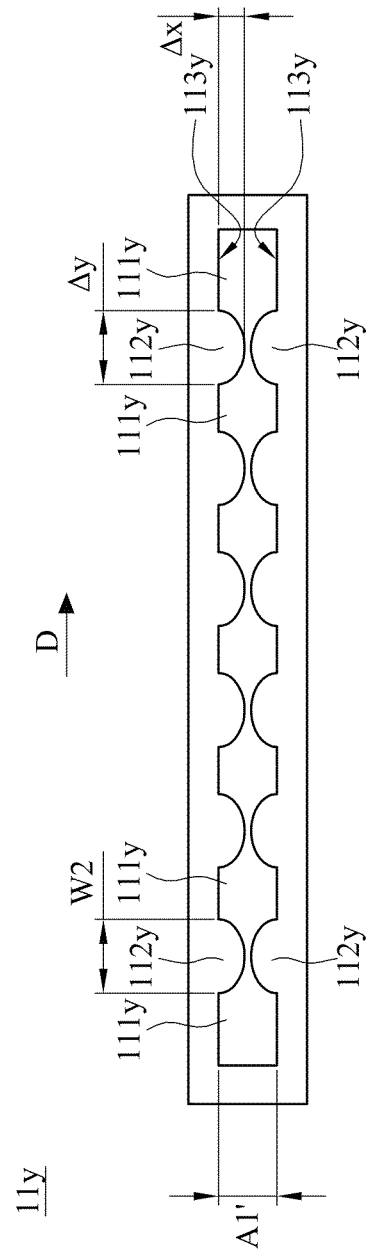
FIG.2C
FIG.2D

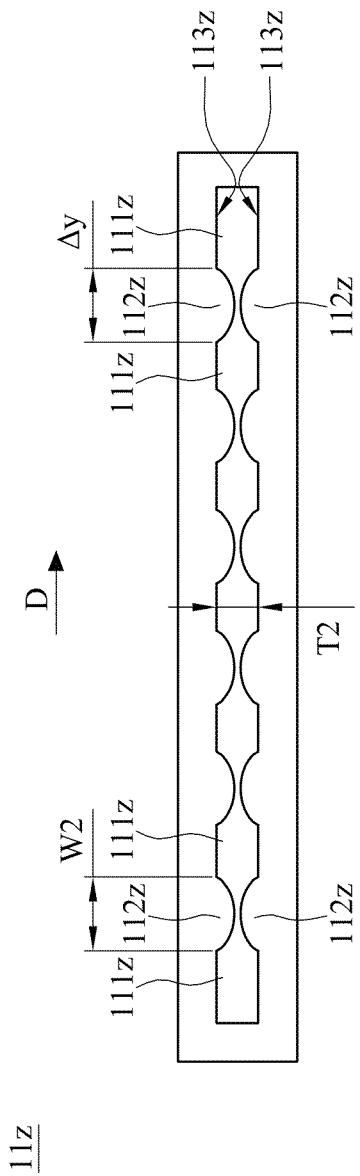
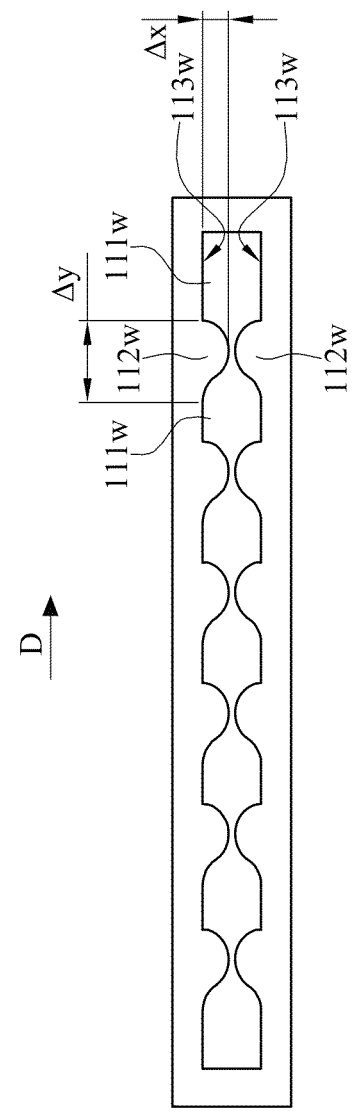
FIG.2E
FIG.2F

DROPLET MANIPULATING DEVICE AND METHOD FOR MANIPULATING DROPLET

CROSS-REFERENCE TO RELATED APPLICATIONS

This non-provisional application claims priority under 35 U.S.C. §119(a) on Patent Application No(s). 102126955 filed in Taiwan, R.O.C. on Jul. 26, 2013, the entire contents of which are hereby incorporated by reference.

TECHNICAL FIELD

The disclosure relates to a droplet manipulating device and a method for manipulating a droplet.

BACKGROUND

In recent years, preventive medicine, early diagnosis, and early treatment have become more important in medical treatment. Specifically, automated instruments, "point of care" (POC), "near patient testing", and molecular detection are being used substantially.

According to a report of global molecular detection, the output of consumption of the global molecular detection market will be increased to 15.5 billion in 2015 and 42.5 billion in 2019. The average growth rate of the market will be up to 11.5% in 2015 and 22.4% in 2019. Therefore, there are enormous opportunities and aspects to be developed in the molecular detection market.

At present time, there have been thousands of biomarkers and biomarker candidates published in journals or patent applications, and the numbers keep increasing. Before the end of February 2010, 913 biomarkers were filed as US patent applications and 76 biomarkers were granted. In addition, 450 biomarkers were applied on clinical molecular medicine. In the future, medical care will pay more attention on the molecular medicine so as to serve personalized medicine, e.g., medical safety screening, medical efficacy tracking and so on. Thus, personalized health care will become a novel trend.

Also, World Health Organization (WHO) proposed some standards for an ideal molecular diagnosis system. According to the standards, each diagnosis should satisfy 7 requirements abbreviated as "ASSURED", which is an acronym for: "Affordable", "Sensitive" (less false negative), "Specific" (less false positive), "User-friendly", "Rapid and robust", "Equipment-free", and "Deliverable to end-users".

Regarding to a standard process of genetic screening in the laboratory, multiple pre-treatments (e.g., forming bonding between blood and the antibodies, cleaning the analyte, forming bonding between the analyte and the antigens) needs to be performed after the analyte is obtained (e.g. whole blood samples, larynx samples and the like) in the standard procedures. Only after the pre-treatments are performed, nucleic acid amplification may be performed (e.g., polymerase chain reaction or methylation-specific polymerase chain reaction). Finally, the genes are identified (e.g. by real time polymerase chain reaction or by electrophoresis). It is easy to find out the above-mentioned process is time-consuming as well as relying on professional technicians and large-scale analytical equipment. In addition, when analytes are complicated (e.g. samples from blood, salvia, or larynx) or have a low concentration, the pre-treatment is more difficult.

In order to improve the diagnoses, analytes are combined with magnetic particles. The user can control the analytes to move in different operating spaces by controlling an external magnetic field. Thus, the analytes combined with the magnetic particles move according to a magnetic force applied by the external magnetic field.

However, in the above controlling method, the distribution of the produced magnetic field is not uniform, so that it is hard to separate the magnetic particles from a droplet, and it is hard to produce a uniform magnetic field covering a larger area. In addition, magnetic particles may improperly adhere to the inner surface of the operating space because of greater friction between the magnetic particles and the operating space.

SUMMARY

According to an embodiment, a droplet manipulating device is disclosed. The droplet manipulating device comprises a flow channel, a first magnetic field generator, and a second magnetic field generator. The flow channel is adapted for accommodating a droplet. The first magnetic field generator comprises two first magnetic field modules opposite to each other. The two first magnetic field modules are at the two opposite sides of the flow channel, respectively, for producing a first magnetic field on the flow channel. The second magnetic field generator is disposed between the two first magnetic field modules. The second magnetic field generator comprises a plurality of second magnetic field coils for producing a second magnetic field on the flow channel. The droplet driven by the first magnetic field and the second magnetic field is in motion in the flow channel.

According to an embodiment, a method for manipulating a droplet is disclosed. The droplet manipulating device comprising a flow channel, a first magnetic field generator, and a second magnetic field generator is provided. The first magnetic field generator comprises two first magnetic field modules opposite to each other. The two first magnetic field modules are at the two opposite sides of the flow channel. The second magnetic field generator is between the two first magnetic field modules. The second magnetic field generator comprises a plurality of second magnetic field coils. A droplet is provided in the flow channel. The droplet comprises at least one magnetic particle. A first magnetic field is produced on the flow channel by the two first magnetic field modules, so that the at least one magnetic particle in the droplet has the direction of magnetic field corresponding to the first magnetic field. A second magnetic field is produced on the flow channel by the plurality of second magnetic field coils, for driving the at least one magnetic particle in the droplet to be in motion in the flow channel.

BRIEF DESCRIPTION OF THE DRAWINGS

The disclosure become more fully understood from the detailed description given herein below along with the accompanying drawings which are for illustration only, thus are not limitative of the disclosure, and wherein:

FIG. 1D is a side view of a droplet manipulating device according to another embodiment of the disclosure;

FIG. 2C is a top view of a flow channel according to another embodiment of the disclosure;

FIG. 2D is a top view of a flow channel according to another embodiment of the disclosure;

FIG. 2E is a top view of a flow channel according to another embodiment of the disclosure;

FIG. 2F is a top view of a flow channel according to another embodiment of the disclosure;

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1A:
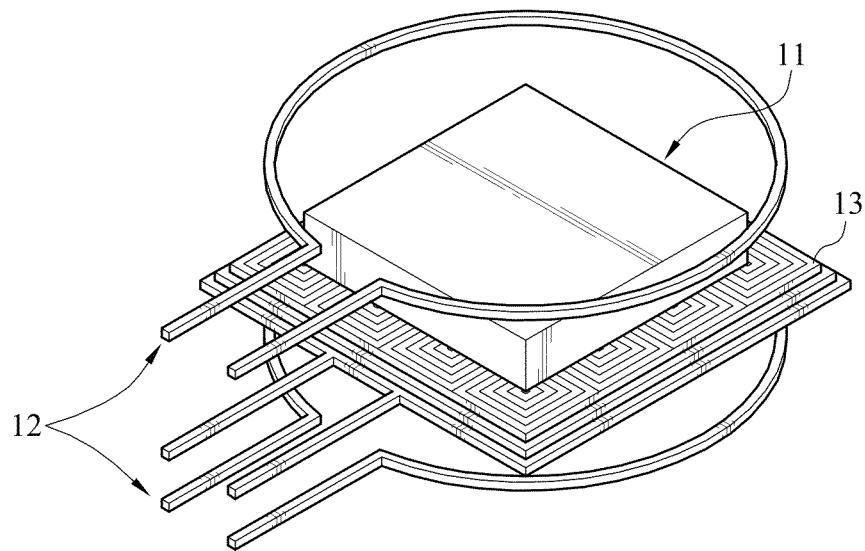
FIG. 1A is a perspective view of a droplet manipulating device according to an embodiment of the disclosure.
Figure 1A:
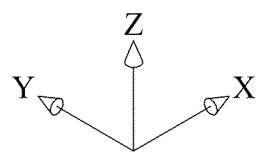
Figure 1B:
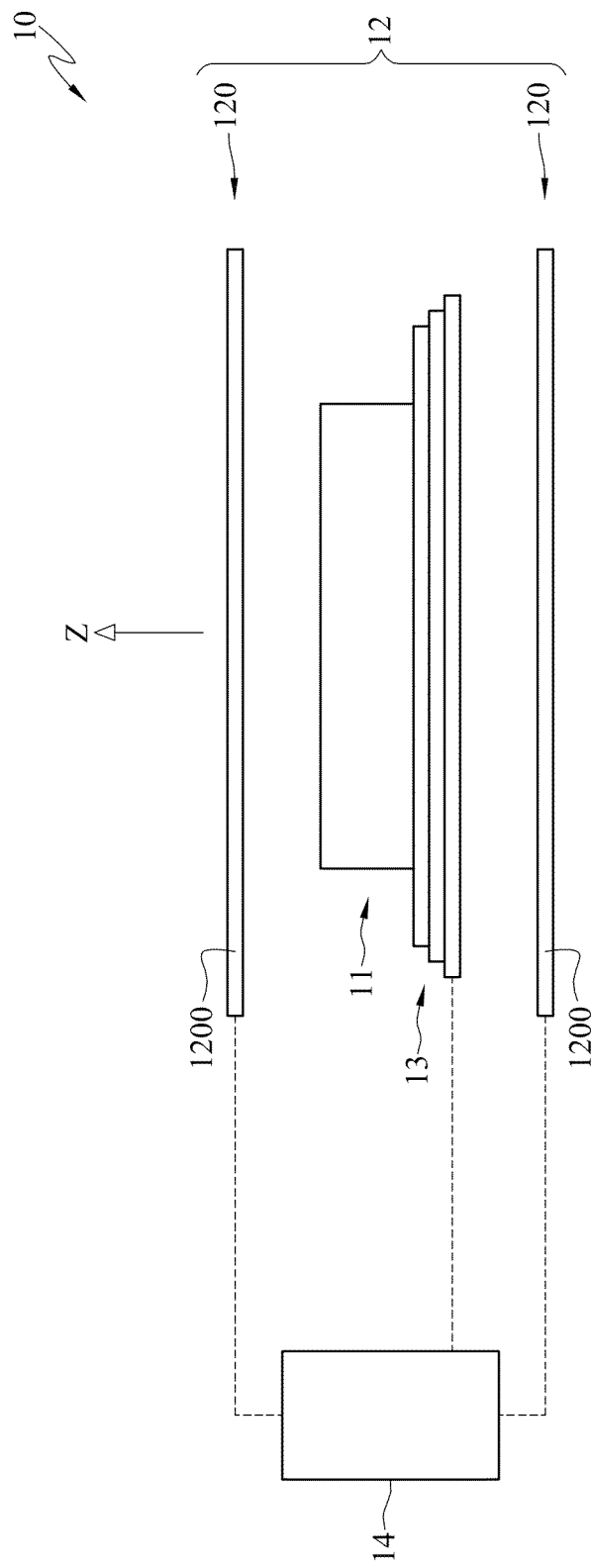
FIG. 1B is a side view of the droplet manipulating device of FIG. 1A.

Please refer to FIGS. 1A and 1B. FIG. 1A is a perspective view of a droplet manipulating device according to an embodiment of the disclosure, and FIG. 1B is a side view of the droplet manipulating device of FIG. 1A. A droplet manipulating device 10 comprises a flow channel 11, a first magnetic field generator 12, and a second magnetic field generator 13. In this embodiment and some other embodiments, the droplet manipulating device 10 further comprises a power controller 14, but the disclosure is not limited thereto.

The flow channel 11 is adapted for accommodating a droplet (not shown). The droplet comprises, for example, at least one magnetic particle. In the following descriptions, the droplet comprising a plurality of magnetic particles is described. The magnetic particles are paramagnetic and are capable of binding with analytes by a specific combination (e.g. combination of antibody-antigen). In other words, the droplet comprises magnetic particles and analytes. The analytes are, for example, antibodies, antigens, proteins, enzymes, ribonucleic acids, deoxyribonucleic acids, cells, or bacterium, but the disclosure is not limited thereto. In some other embodiments, the droplet further comprises surfactants so that the magnetic particles are mixed in the droplet more uniformly. In this embodiment, the surfactants are hydrophobic surfactants, such as sorbitan oleate (span 80), but the disclosure is not limited thereto. In addition, an environmental liquid is contained in the flow channel 11 and is, for example, mineral oils or silicone oils.

In addition, the user can accommodate different diagnosing liquid in the flow channel 11 according to his/her needs. For instance, when the user needs to detect whether the analytes have a certain DNA sequence, the user can accommodate another DNA sequence, which is complementary to the certain DNA sequence, in the flow channel 11. Therefore, when the analytes have the certain DNA sequence, the two complementary DNA sequences bind together by hydrogen bonding, so as to detect the analytes having the certain DNA sequence.

In this embodiment and some other embodiments, the inner surface of the flow channel 11 is a hydrophobic surface. Thereby, the contact angle between the droplet and the inner surface of the flow channel 11 is increased, such that the droplet may not substantially adhere on the inner surface of the flow channel 11, so as to control the movement of the droplet conveniently.

Figure 2A:
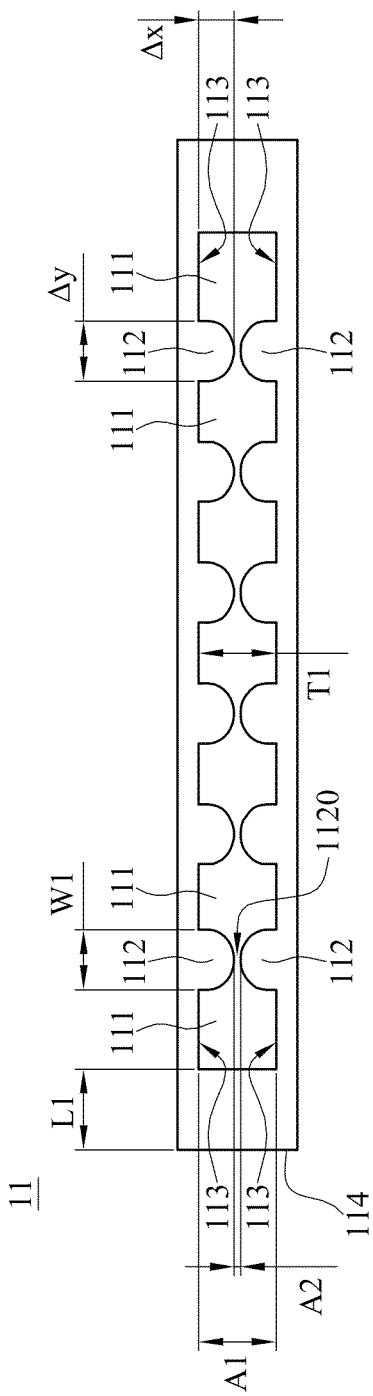
FIG. 2A is a top view of the flow channel of FIG. 1A.
Figure 2B:
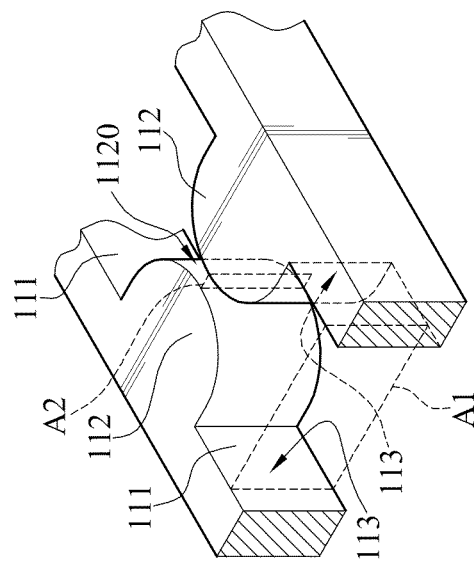
FIG. 2B is a sectional view of part of the flow channel of FIG. 2A.

Please refer to FIGS. 1A, 11B, and 2A-2F. FIG. 2A is a top view of the flow channel of FIG. 1A, FIG. 2B is a sectional view of part of the flow channel of FIG. 2A, FIG. 2C is a top view of a flow channel according to another embodiment of the disclosure, FIG. 2D is a top view of a flow channel according to another embodiment of the disclosure, FIG. 2E is a top view of a flow channel according to another embodiment of the disclosure, and FIG. 2F is a top view of a flow channel according to another embodiment of the disclosure. In the embodiment, the flow channel 11 extends along the horizontal direction. In FIGS. 1A, 1B, and 2A-2F, the flow channel 11 has a single diagnosing direction, but the disclosure is not limited thereto. In some other embodiments, the flow channel has two diagnosing directions, which intersect with each other.

In this and some other embodiments, the flow channel 11 comprises a plurality of operating spaces 111 and at least one separating unit 112 corresponding to the plurality of operating spaces 111. The separating unit 112 is disposed between two operating spaces 111 which are adjacent to each other. The separating unit 112 is, for example, a bump protruding from the two opposite sidewalls 113 of the flow channel 11. The width W1 of the bump is 3 millimeters (mm), and the distance T1 between the two sidewalls 113 is 6 mm. The separating unit 112 has a gap 1120 for the operating spaces 111 connecting with each other. Each of the operating spaces 111 has a cross sectional area A1 along the longitudinal direction (namely, radial direction), and the gap 1120 has a cross sectional area A2 along the longitudinal direction. The cross sectional area A1 is greater than the cross sectional area A2 (as shown in FIG. 2B). In addition, the diameter of the gap 1120 is between 0.3 mm and 0.7 mm. However, the above dimensions (e.g. width, distance, diameter . . . ) do not limit to the disclosure. The user can accommodate different liquids in different operating spaces 111, such that the user can perform different operations (e.g. pre-treatment, detection, or post-treatment) in different operating spaces 111.

In FIG. 2A, the minimum distance L1 between a starting end 114 of the flow channel 11 and the operating space 111 is greater than or equal to 6 mm. In some other embodiments, the minimum distance L2 between the starting end 114x of the flow channel 11x and the operating space 111x is 4 mm (as shown in FIG. 2C), so that the flow channel 11x has a smaller size. In some other embodiments, the width W2 of the bump of the separating unit 112y is 3.5 mm (as shown in FIG. 2D), so that the variation rate ($\Delta X/\Delta Y$) of the separating unit 112y protruding from the sidewalls 113y is smaller. Therefore, when the droplet moves from an operating space 111y to another operating space 111y along a direction D, the drag force (namely, the force which the inner surface of the flow channel prevents the droplet moving along the flow channel, and is generated because of, for example, friction of the inner surface) from the flow channel 11y to the droplet is decreased, and the droplet moves (along the direction D) more smoothly. In some other embodiments, the distance T2 between the two sidewalls 113z is 4 mm (as shown in FIG. 2E), so that the distance T2 is decreased and the droplet moves from an operating space 111z to another operating space 111z along the direction D more smoothly. Therefore, the separating unit 112z does not impede the droplet moving from one operating space 111z to another operating space 111z, so the droplet can move more smoothly because the distance between the two sidewalls 113z is smaller. In some other embodiments, the separating unit 112w is a fish-scale-shaped structure protruding from the two sidewalls 113w of the flow channel 11w (as shown in FIG. 2F). In other words, the variation rate ($\Delta X/\Delta Y$) of the separating unit 112w protruding from the sidewalls 113w increases along the direction D, such that the droplet moves from one operating space 111w to another operating space 111w more smoothly.

Figure 2G:
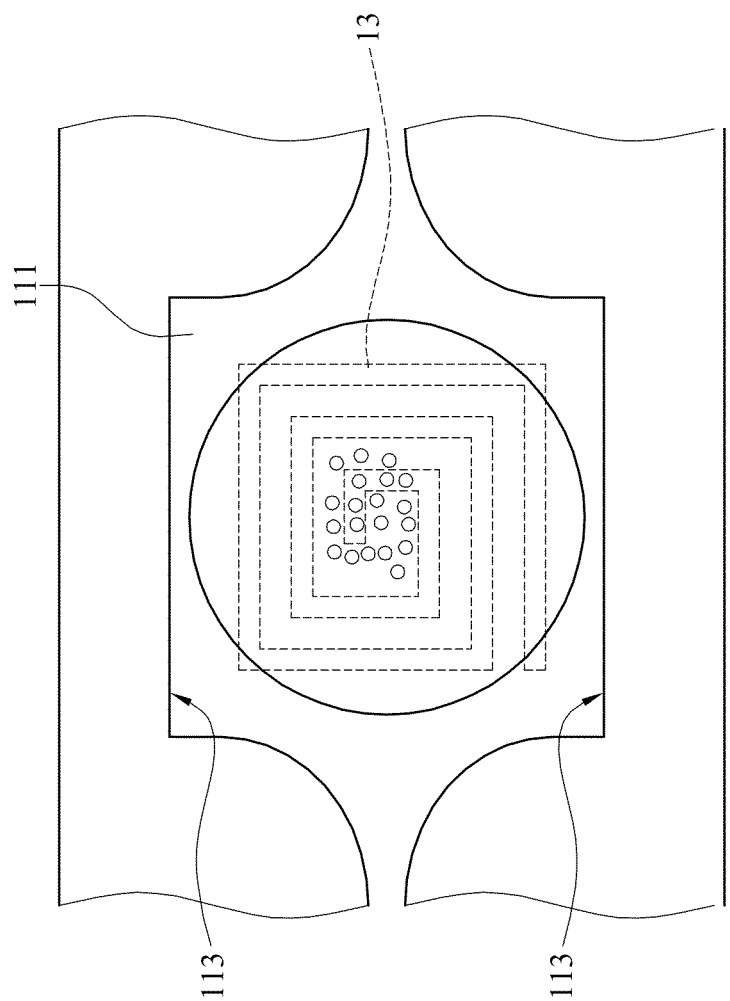
FIG. 2G is a top view of an operating space of FIG. 2A accommodating a droplet.
Figure 2H:
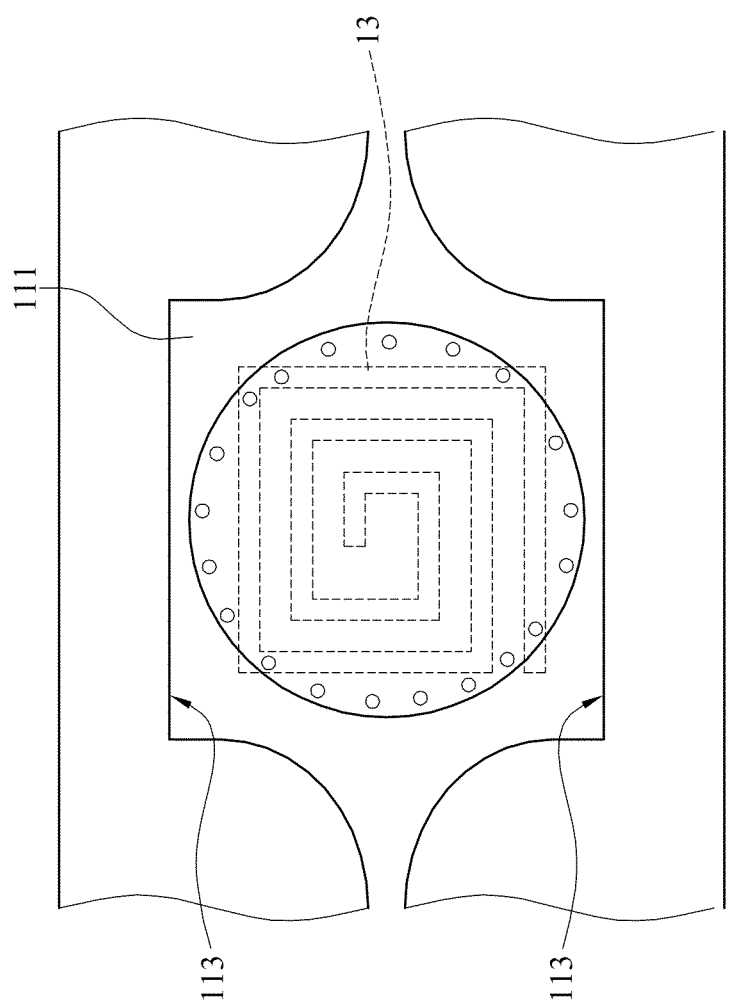
FIG. 2H is another top view of an operating space of FIG. 2A accommodating a droplet.

Please refer to FIGS. 2A and 2G-2H. FIG. 2G is a top view of an operating space of FIG. 2A accommodating a droplet, FIG. 2H is another top view of an operating space of FIG. 2A accommodating a droplet. In this embodiment, the distance T1 between the two sidewalls 113 corresponds to the diameter of the droplet. The sidewalls 113 are capable of confining the droplet in the operating space 111. Therefore, the droplet is well positioned in the operating space 111 and the position of the droplet corresponds with the second magnetic field generated by the second magnetic field generator 13. Since the position of the droplet corresponds with the second magnetic field, the dispersion of the magnetic particles inside the droplet is more uniform when the magnetic particles are concentrated in the droplet (FIG. 2G) and when the magnetic particles are dispersed in the droplet (FIG. 2H).

Figure 1C:
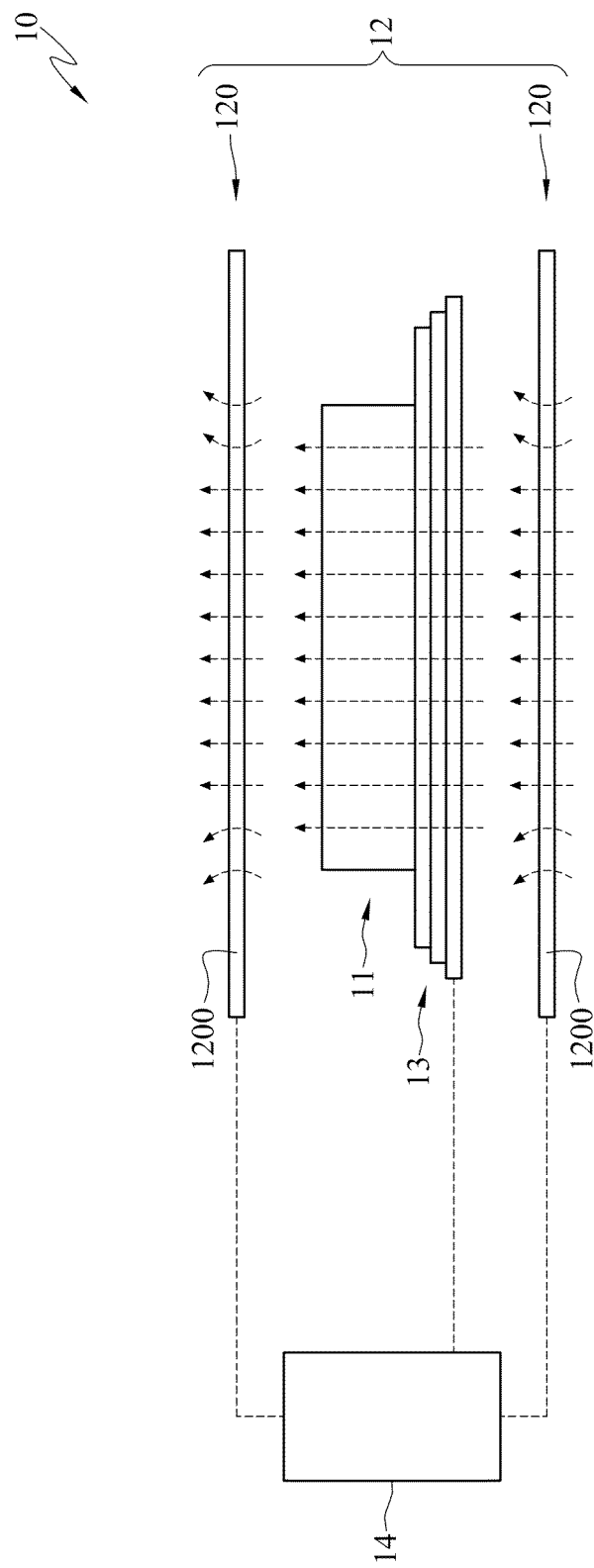
FIG. 1C is a side view of the droplet manipulating device of FIG. 1A under an operating status.
Figure 1E:
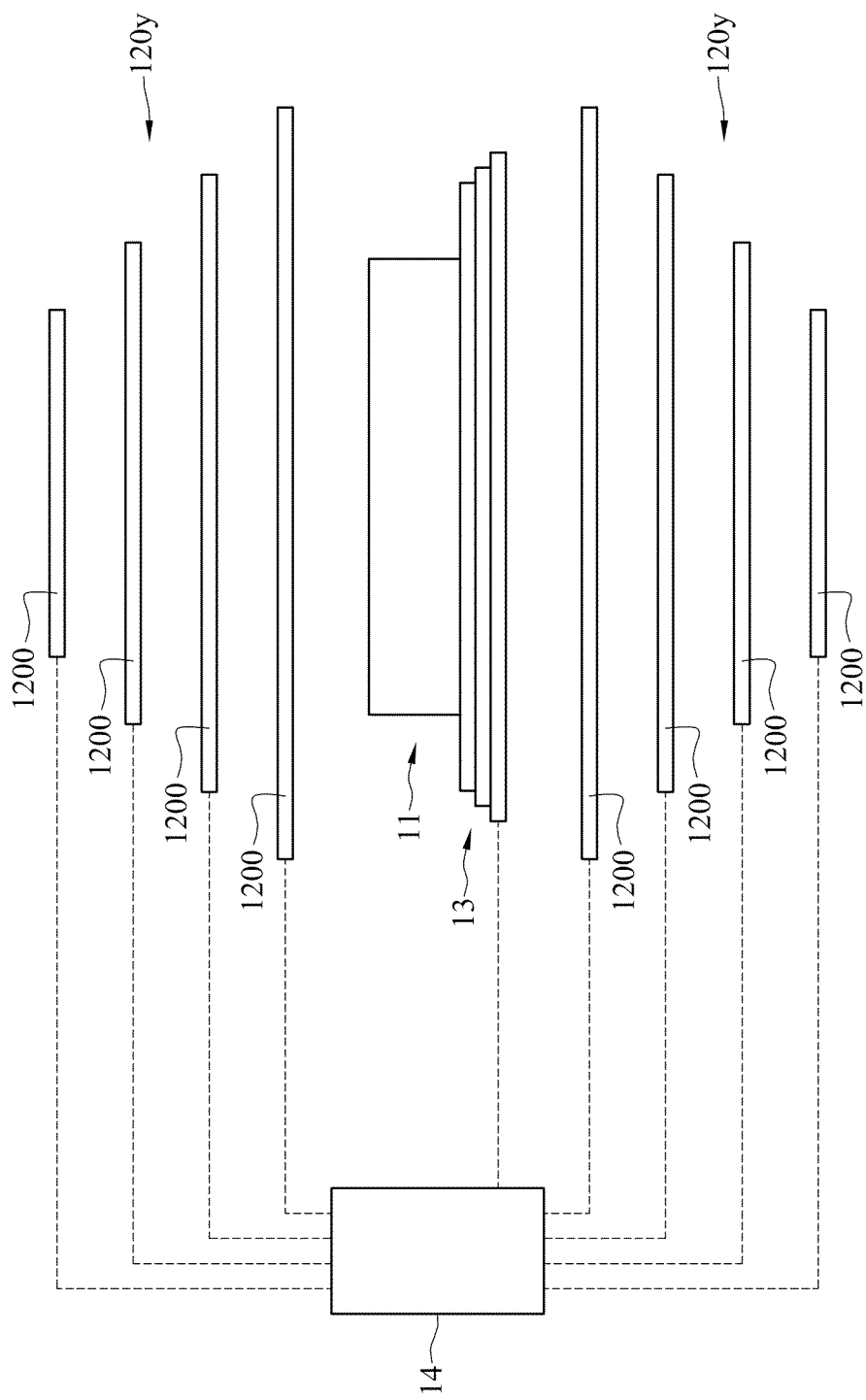
FIG. 1E is a side view of a droplet manipulating device according to another embodiment of the disclosure.
Figure 1F:
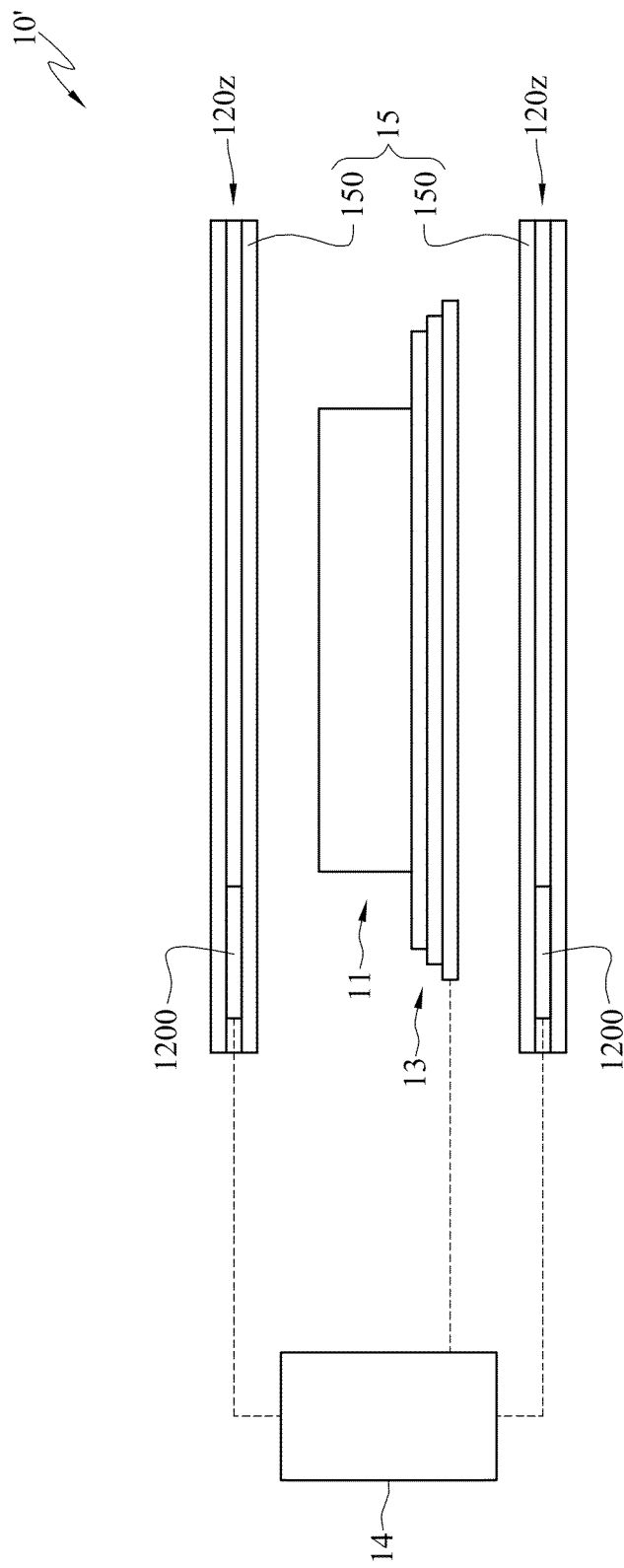
FIG. 1F is a side view of a droplet manipulating device according to another embodiment of the disclosure.
Figure 1G:
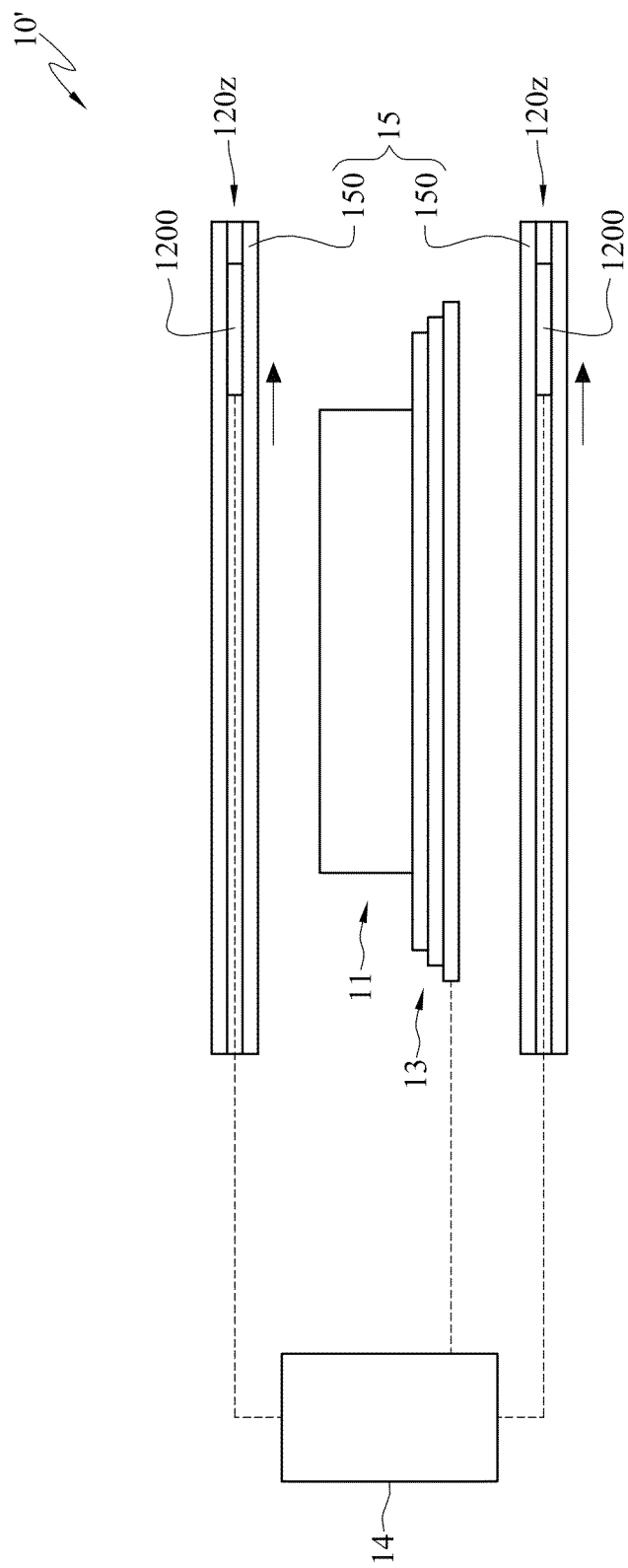
FIG. 1G is another side view of the droplet manipulating device of FIG. 1F.
Figure 1H:
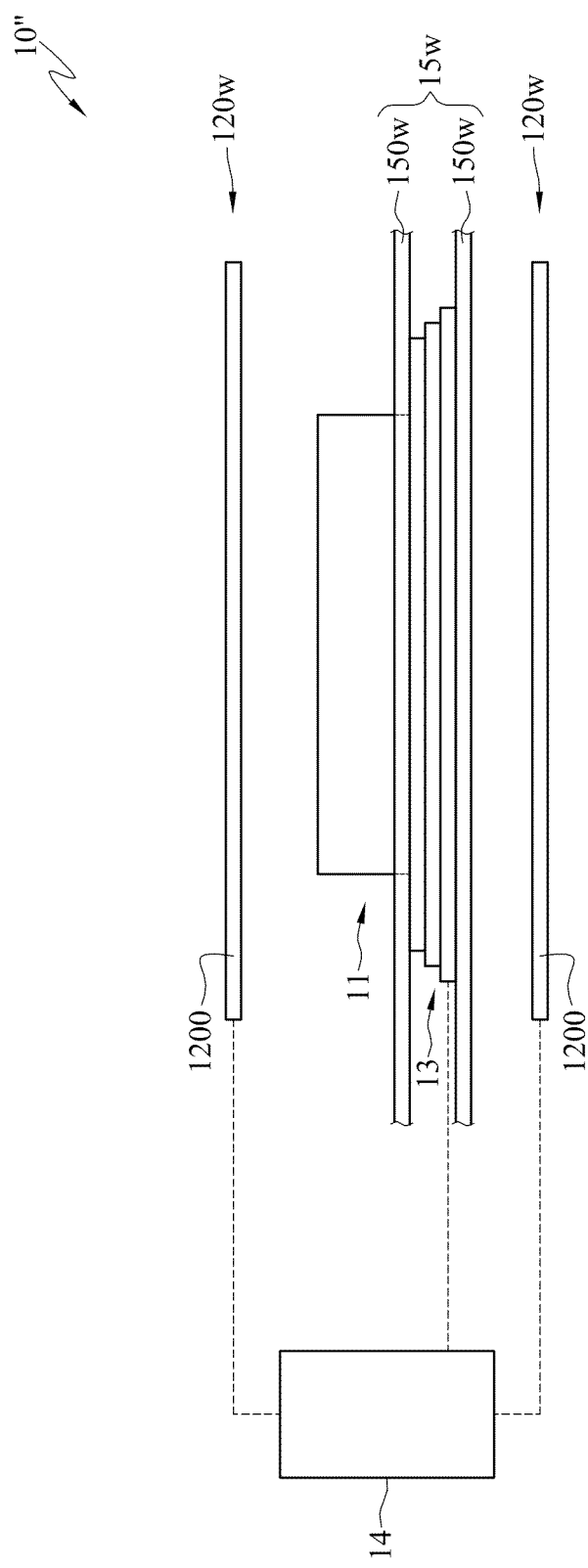
FIG. 1H is a side view of a droplet manipulating device according to another embodiment of the disclosure.

Please refer to FIGS. 1A-1H. FIG. 1C is a side view of the droplet manipulating device of FIG. 1A under an operating status, FIG. 1D is a side view of a droplet manipulating device according to another embodiment of the disclosure, FIG. 1E is a side view of a droplet manipulating device according to another embodiment of the disclosure, FIG. 1F is a side view of a droplet manipulating device according to another embodiment of the disclosure, FIG. 1G is another side view of the droplet manipulating device of FIG. 1F, and FIG. 1H is a side view of a droplet manipulating device according to another embodiment of the disclosure. The first magnetic field generator 12 comprises two first magnetic field modules 120. In this embodiment, the two first magnetic field modules 120 are opposite to each other and are symmetrical to each other according to the flow channel 11, but the disclosure is not limited thereto. Each of the first magnetic field modules 120 has at least one first magnetic field coil 1200, respectively. In this embodiment, each of the first magnetic field modules 120 has one first magnetic field coil 1200, respectively. However, the number of the first magnetic field coils 1200 does not limit to the disclosure. In some other embodiments, each of the first magnetic field modules 120x has two first magnetic field coils 1200 (as shown in FIG. 1D), respectively. In some other embodiments, each of the first magnetic field modules 120y has four first magnetic field coils 1200 (as shown in FIG. 1E), respectively. In some other embodiments, the radii of the first magnetic field coils 1200 are different.

The first magnetic field coils 1200 having greater radii are disposed between the first magnetic field coils 1200 having smaller radii.

In some other embodiments, the droplet manipulating device 10' further comprises a first rail module 15 disposed at the two opposite sides of the flow channel 11. The first rail module 15 comprises two rails 150 opposite to each other and disposed at the two opposite sides of the flow channel 11. The first magnetic field modules 120z are movably disposed on the rails 150 for moving relative to the flow channel 11 (as shown in FIGS. 1F and 1G). The first magnetic field modules 120z move corresponding to the position of the droplet. The first magnetic field, which is produced by the first magnetic field modules 120z, covers the range where the droplet moves. In other words, the magnetic field produced by the first magnetic field modules 120z moves according to the position of the droplet. However, the moving direction of the first magnetic field modules 120z does not limit the disclosure. In some other embodiments, the first magnetic field modules 120z move along a line (1D motion), and in some other embodiments, the first magnetic field modules 120z move along a plane (2D motion).

In addition, the first magnetic field modules 120z moving along the rail 150 corresponding to the position of the droplet does not limit to the disclosure. Please refer to FIG. 1H, the flow channel 11 and the second magnetic field generator 13 of the droplet manipulating device 10" are disposed on the rail 150w of the second rail 15w. In other words, the flow channel 11 and the second magnetic field generator 13 are capable of moving along the rail 150w while the droplet moves.

In some other embodiments, the droplet manipulating device comprises both the first rail module and the second rail module, such that the first magnetic field module and the flow channel, as well as the second magnetic field generator are capable of moving relative to each other along the first rail module and the second slide module.

In FIGS. 1F to 1H, the relative positions of the first magnetic field modules 120z and 120w, the flow channel 11 and the second magnetic field generator 13 are changed by the first rail module 15 and/or the second rail module 15w, so the first magnetic field is only produced at the position of the droplet. Thus, the first magnetic field modules 120z and 120w (and the produced first magnetic field) do not need to cover the whole droplet manipulating device 10' and/or 10". Accordingly, the first magnetic field modules 120z and 120w can have a smaller size, and the first magnetic field modules 120z and 120w only need less power to operate.

Figure 1I:
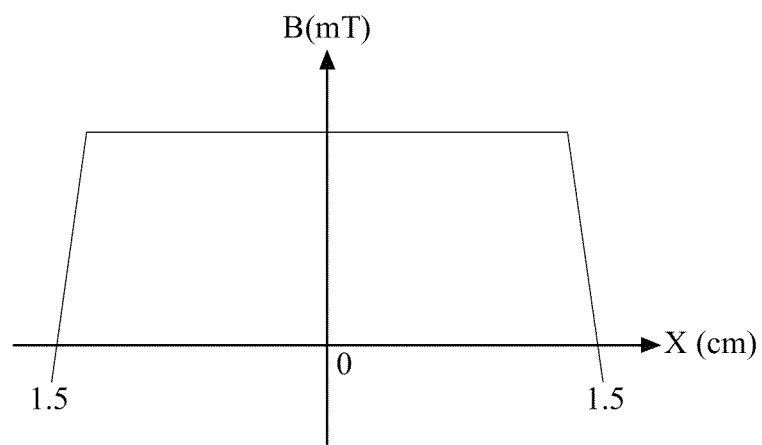
FIG. 1I is a graph of the magnetic field of the droplet manipulating device of FIG. 1A under an operating status.
Figure 3A:
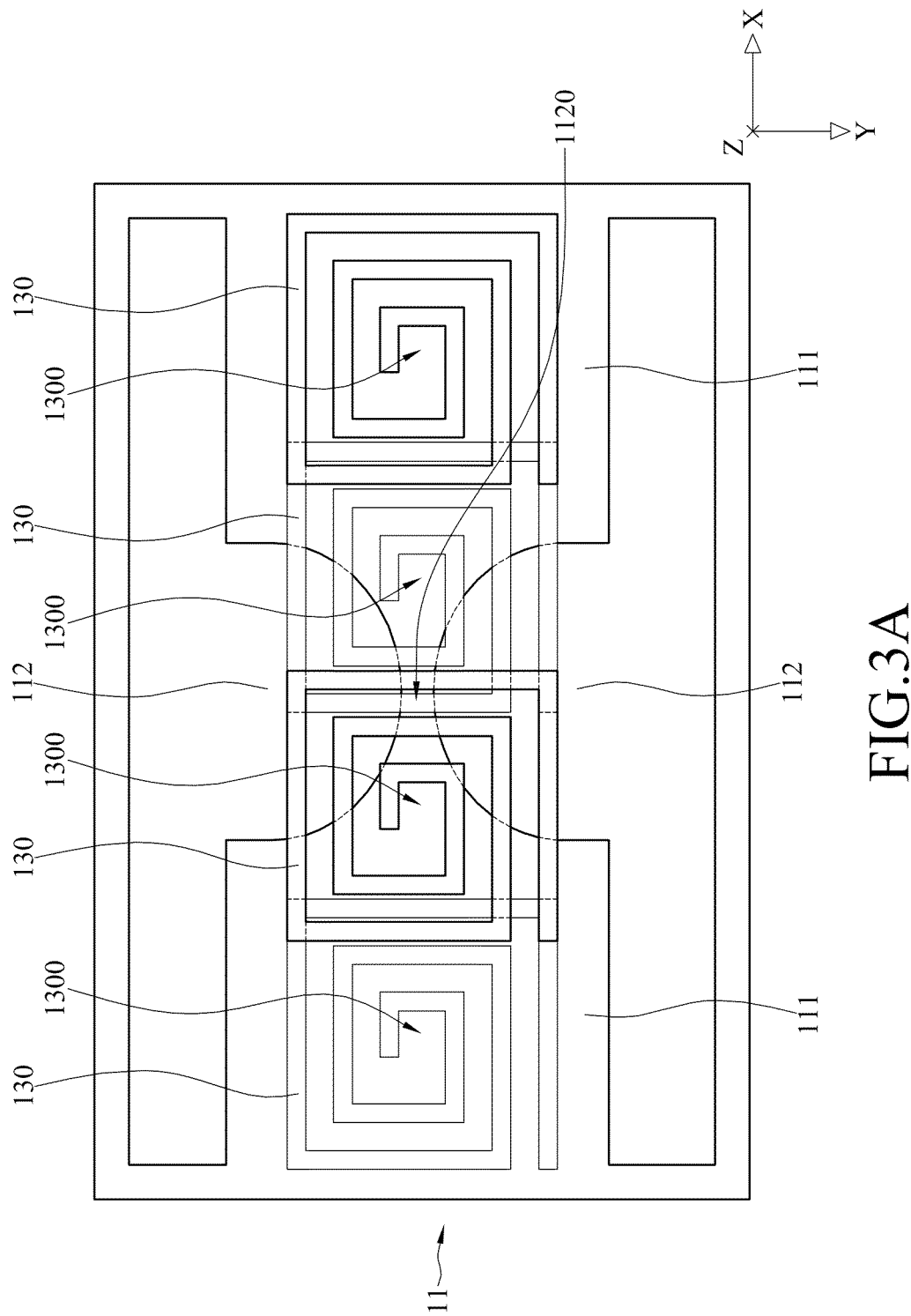
FIG. 3A is a top view of part of the droplet manipulating device of FIG. 1A.
Figure 3B:
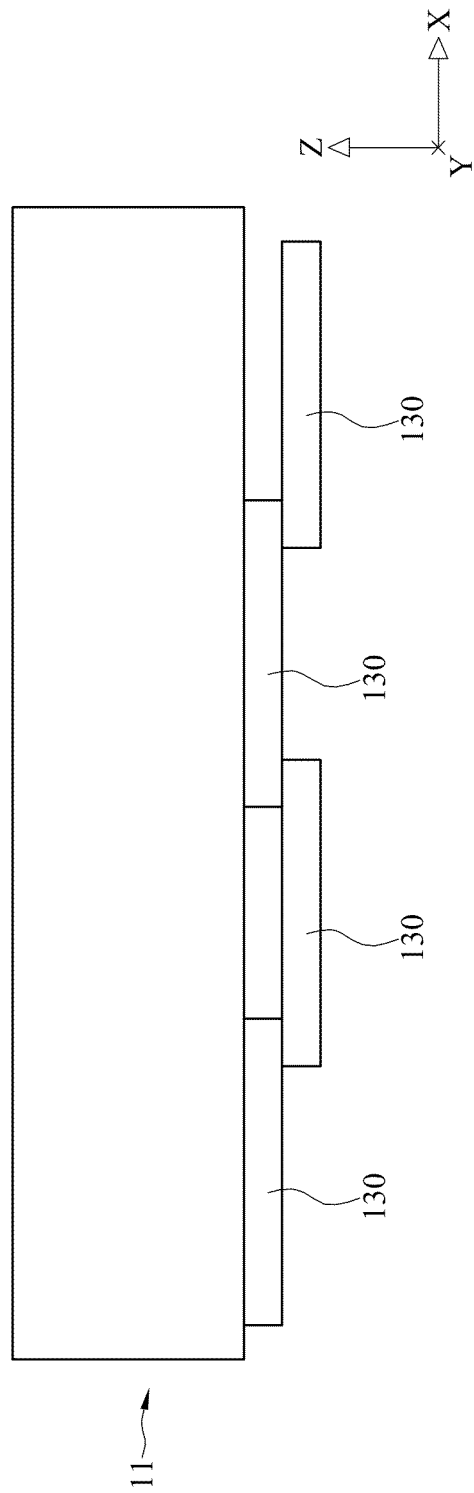
FIG. 3B is a side view of the flow channel and the second magnetic field generator of FIG. 3A.

Please refer to FIGS. 1A-1C, 1I, 2A, 3A and 3B. FIG. 1I is a graph of the magnetic field of the droplet manipulating device of FIG. 1A under an operating status, FIG. 3A is a top view of part of the droplet manipulating device of FIG. 1A, and FIG. 3B is a side view of the flow channel and the second magnetic field generator of FIG. 3A. The first magnetic field modules 120 are disposed at the top side and the bottom side of the flow channel 11, respectively. In other words, the flow channel 11 is disposed between the two first magnetic field modules 120 along the perpendicular direction (namely, direction Z). The first magnetic field modules 120 are adapted for producing a first magnetic field. The first magnetic field is uniformly distributed in each of the operating spaces 111 at the same horizontal plane (which represents XY plane or planes parallel to XY plane of FIG. 3A) of the operating space 111, the intensity of magnetism of the first magnetic field is identical. Also, the vertical planes (which are perpendicular to XY plane of FIG. 3A) having identical distances to the separating unit 112 have identical intensity of magnetism of the first magnetic field.

The second magnetic generator 13 comprises a plurality of second magnetic field coils 130 disposed between the two first magnetic field modules 120 and arranged in an array. The second magnetic field coils 130 are adapted for producing a second magnetic field. Each of the first magnetic field modules 120 and each of the second magnetic field coils 130 are, for example, print circuit boards, electromagnets, or micro coils, but the disclosure is not limited thereto.

In this embodiment, the intensity of magnetism of the first magnetic field and the second magnetic field along the direction Z are between 20 microtesla (mT) and 80 mT. In a 4 cm×4 cm area, the intensity of magnetism of the first magnetic field and the second magnetic field along the direction Z are uniform. Also, the gradient of the intensity of magnetism of the first magnetic field and the second magnetic field along the direction X-Y is 10 mT. However, the above intensity of magnetism does not limit to the disclosure, the user can adjust the intensity of magnetism according to his/her needs.

Further, each of the operating spaces 111 corresponds to at least two second magnetic field coils 130, and the separating unit 112 is disposed between two second magnetic field coils 130 which are adjacent to each other. In addition, each of the second magnetic field coils 130 has a magnetic field center 1300. The projection of the magnetic field center 1300 on the flow channel 11 is not projected on the gap 1120. Therefore, the intensity of magnetism of second magnetic field at each operating spaces 111 can be controlled by at least two second magnetic field coils 130. Also, the intensity of magnetism of second magnetic field at each gaps 1120 can be controlled by at least two second magnetic field coils 130.

Furthermore, the gap 1120 of the separating unit 112 is disposed between two magnetic field centers 1300, which are adjacent to each other. In other words, the projection of the magnetic field center 1300 along the direction Z and the projection of the gap 1120 along the direction Z are at different positions. Since the gap 1120 is between the two adjacent magnetic field centers 1300, the droplet can move from an operating space 111 to another operating space 111 by controlling the first magnetic field and the second magnetic field (as shown in FIG. 3A).

In this embodiment, the second magnetic field coils 130 are disposed on different horizontal planes along the direction Z and are arranged alternately (as shown in FIG. 3B). In some other embodiments, the second magnetic field coils 130 are on the same horizontal plane along the direction Z.

The power controller 14 is electrically connected to the first magnetic field generator 12 and the second magnetic field generator 13 and adapted for controlling the magnitude of the current so as to control the intensity of the magnetism produced by the first magnetic field generator 12 and the second magnetic field generator 13. Furthermore, the power controller 14 is adapted for controlling the variation of the intensity of magnetism of the first magnetic field and the second magnetic field with time (for example, at different time points, or the direction of magnetic field of the second magnetic field is the same with the first magnetic field, the direction of magnetic field of the second magnetic field is opposite to the first magnetic field, or the second magnetic field is 0).

Therefore, the interaction between the first magnetic field and the second magnetic field is controlled by controlling the first magnetic field produced by the first magnetic field generator 12 and the second magnetic field produced by the second magnetic field generator 13 (as shown in FIG. 1C). The user can adjust the distribution of the magnetic field and the gradient of the magnetic field (as shown in FIG. 1I) so that the droplet can be transported, mixed, separated, agitated, trapped, or split. Therefore, transport, mix, separation, agitation, or cut of the droplet can be achieved. Since the motion of the droplet is controlled by the interaction between the two magnetic fields, and the produced magnetic fields are more uniform, so that it is more convenient to control the motion of the magnetic particles.

Figure 1J:
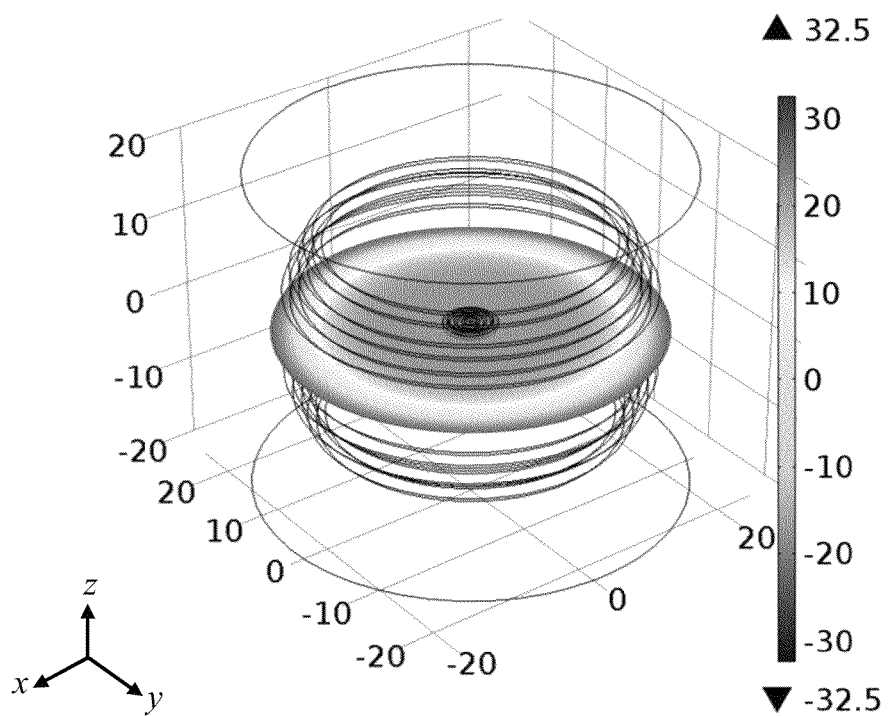
FIG. 1J is a graph of the magnetic field of the droplet manipulating device under an operating status.
Figure 1K:
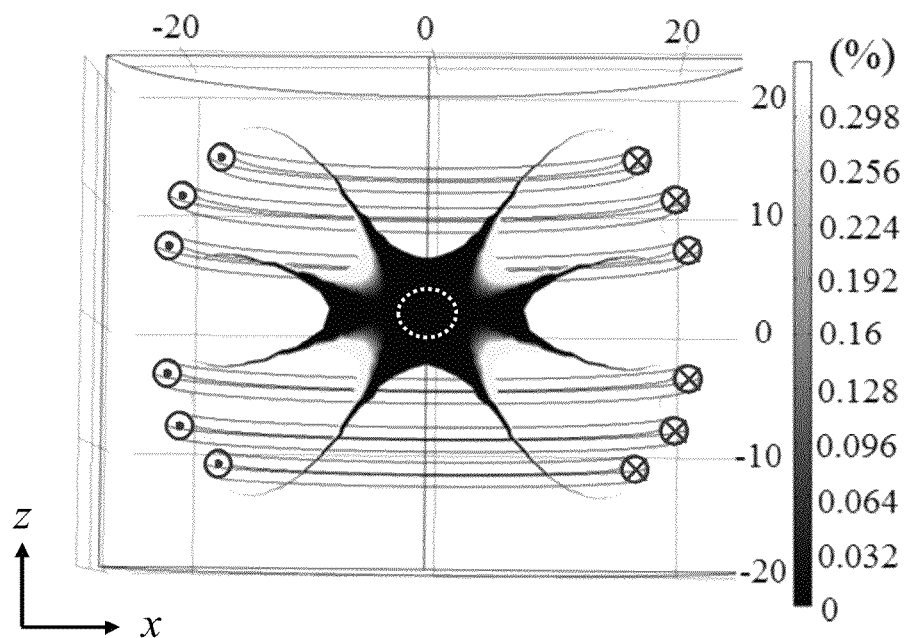
FIG. 1K is a graph of the magnetic field of the droplet manipulating device along xz-plane under an operating status.

Please refer to FIG. 1J, which is a graph of the magnetic field of the droplet manipulating device under an operating status. The grayscale represents the magnitude of the magnetism. As shown in FIG. 1J, the magnetism is uniformly formed at the xy-plane. In fact, the magnetism is uniformly formed at each planes perpendicular to the z-axis.

Please refer to FIG. 1J, which is a graph of the magnetic field of the droplet manipulating device along xz-plane under an operating status. The grayscale represents the difference of the magnetism between X-axial and Y-axial. As shown in FIG. 1J, the difference of the magnetism is small, and the magnetism is uniformly formed.

The following further describes how to control the motion of the droplet in the flow channel, the manipulation of the droplet manipulating device 10 of FIG. 1B, and controlling the motion of a droplet in the flow channel. However, the amount of the droplet does not limit to the disclosure. In some other embodiments, the motion of a plurality of droplets is controlled by the user. In addition, the droplet manipulating device 10 of FIG. 1B does not limit the disclosure. In some other embodiments, the user can adapt the droplet manipulating device 10' of FIG. 1F or the droplet manipulating device 10" of FIG. 1G. In the embodiments of FIG. 1F, the first magnetic field modules 120z moves according to the position of the droplet. Thus, the position of the magnetic field, which is produced by the first magnetic field modules 120z, varies according to the position of the droplet.

Figure 4A:
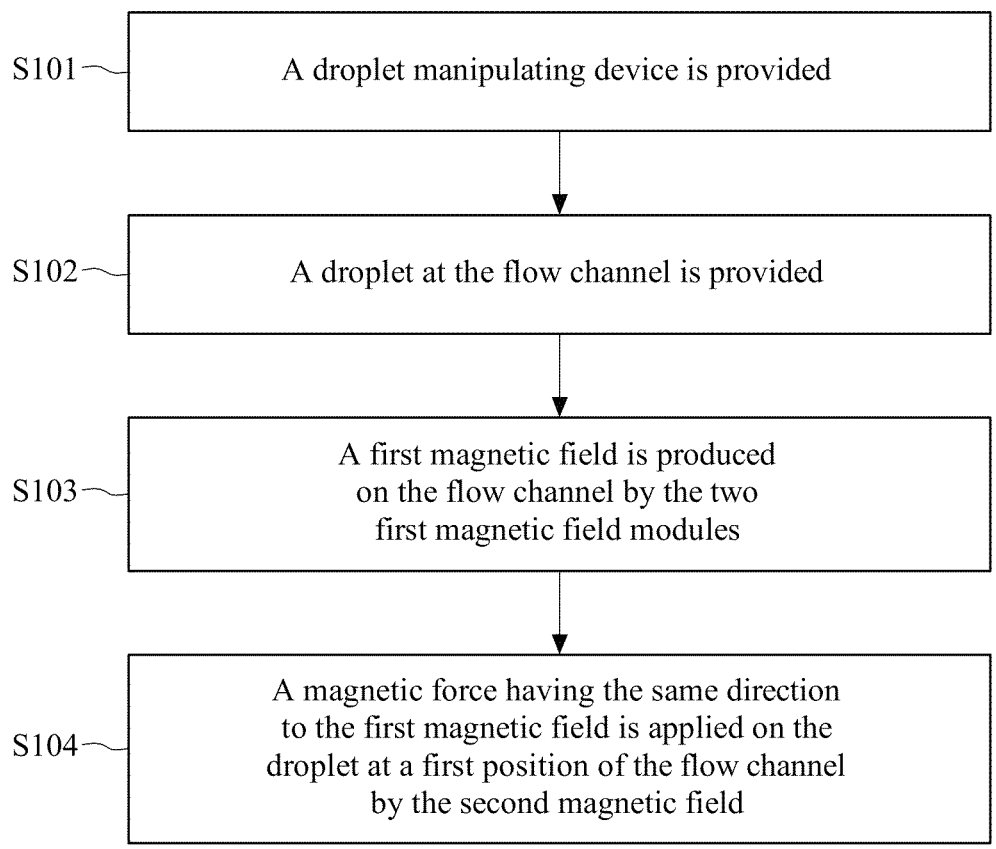
FIG. 4A is a flow chart of a method for manipulating droplet according to an embodiment of the disclosure.
Figure 4B:
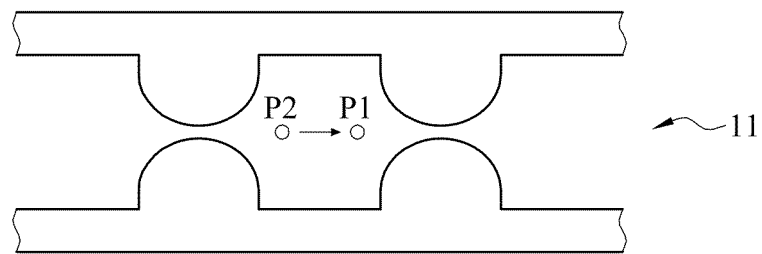
FIG. 4B is a top view of the flow channel of the droplet manipulating device of FIG. 4A.
Figure 4C:
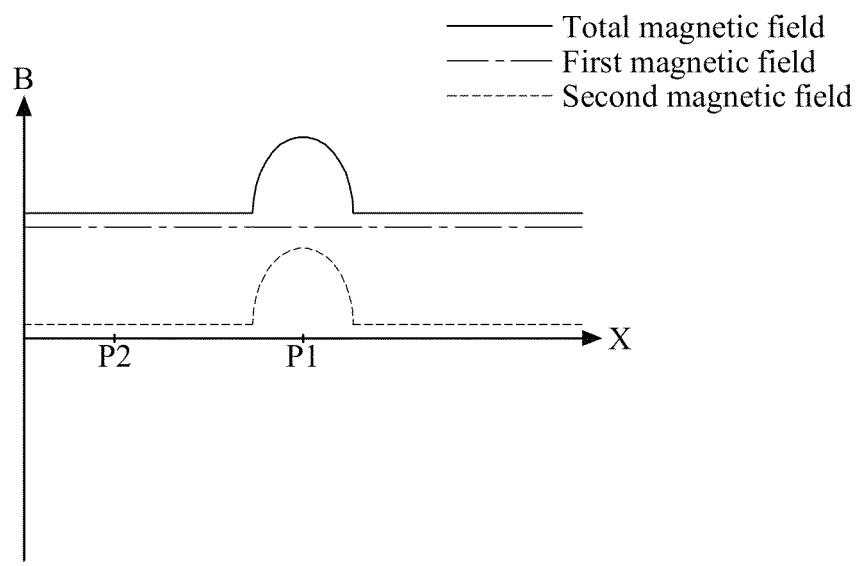
FIG. 4C is a graph of the magnetic field of Step S104 of FIG. 4A.

Please refer to FIGS. 1A, 4A-4C. FIG. 4A is a flow chart of a method for manipulating the droplet according to an embodiment of the disclosure, FIG. 4B is a top view of the flow channel of the droplet manipulating device of FIG. 4A, and FIG. 4C is a graph of the magnetic field of Step S104 of FIG. 4A. The embodiments of FIGS. 4A to 4C describe how to control the movement of the droplet in the flow channel 11.

First, a droplet manipulating device 10 is provided (S101). The structure of the droplet manipulating device 10 is described above, so the structure of the droplet manipulating device 10 is not described again.

Then, a droplet at the flow channel 11 is provided (S102). The droplet comprises, for example, magnetic particles. In some embodiments, the magnetic particles combine with the analytes, and in some other embodiments the magnetic particles do not combine with the analytes.

Afterwards, a first magnetic field is produced on the flow channel 11 by the two first magnetic field modules 120 (S103), so that the droplet has the direction of magnetic field corresponding to the first magnetic field. Since the magnetic particles in the droplet are paramagnetic, the magnetic particles in the droplet have the direction of magnetic field corresponding to the first magnetic field when the first magnetic field is produced on the flow channel 11 by the two first magnetic field modules 120. Also, the dispersion of the magnetic particles in the droplet is more uniform when the first magnetic field is produced on the droplet.

Then, a magnetic force having the same direction to the first magnetic field is applied on the droplet at a first position P1 of the flow channel 11 by the second magnetic field (S104) for driving the droplet to move from a second position P2, which is different from the first position P1, to the first position P1 (as shown in FIG. 4B). When the magnetic force having the same direction to the first magnetic field is applied on the droplet at the first position P1 of the flow channel 11 by the second magnetic field, the summation of the first magnetic field and the second magnetic field at the first position P1 is greater than at the second position P2, and the attractive force at the first position P1 is greater than the attractive force at the second position P2, so that the droplet is attracted from the second position P2 to the first position P1. The distribution of the magnetic fields produced by the droplet manipulating device 10 at Step S104 is shown in FIG. 4C. FIGS. 4A-4C describe how to control the motion of the droplet inside one operating space 111. The following further describes how to control the motion of the droplet in different operating spaces 111 (e.g. the droplet moves from one operating space to another operating space).

Figure 5A:
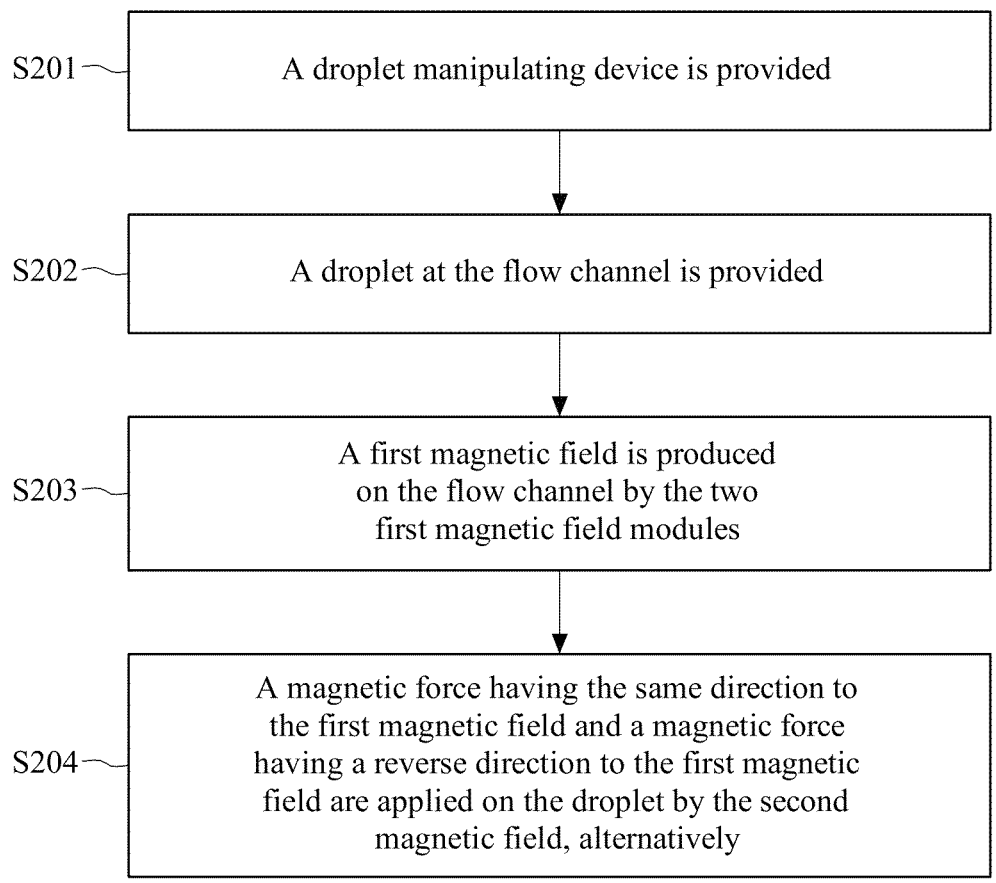
FIG. 5A is a flow chart of a method for manipulating the droplet according to another embodiment of the disclosure.
Figure 5B:
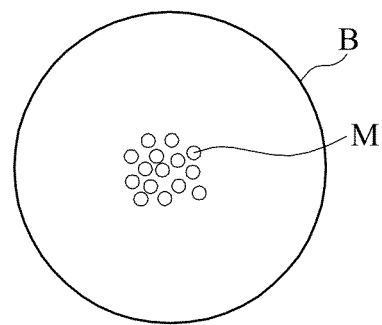
FIG. 5B is a top view the distribution of the magnetic particle in the droplet of Step S204 of FIG. 5A.
Figure 5C:
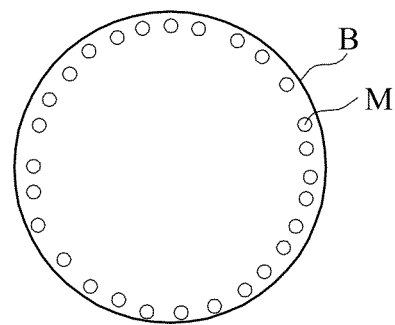
FIG. 5C is a top view of the distribution of the magnetic particle in the droplet of Step S204 of FIG. 5A.
Figure 5D:
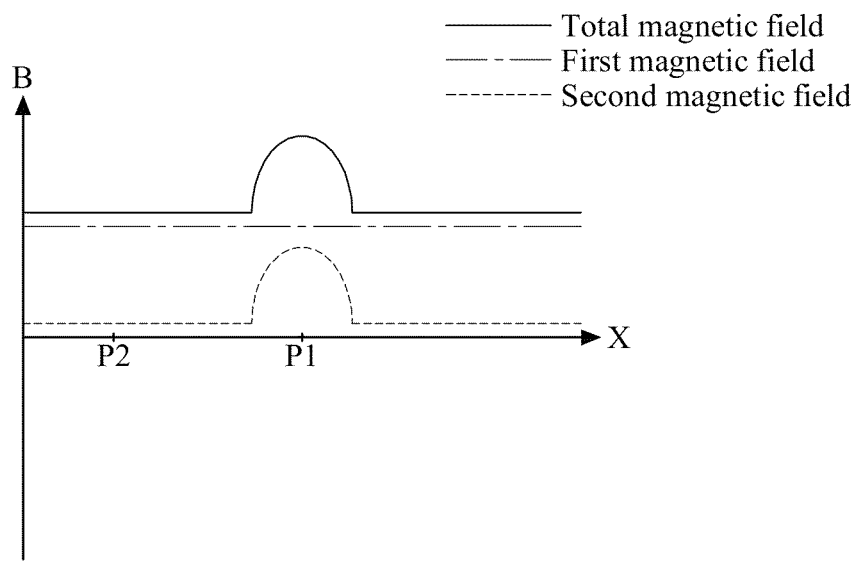
FIG. 5D is a graph of the magnetic field of Step S204 of FIG. 5A.
Figure 5E:
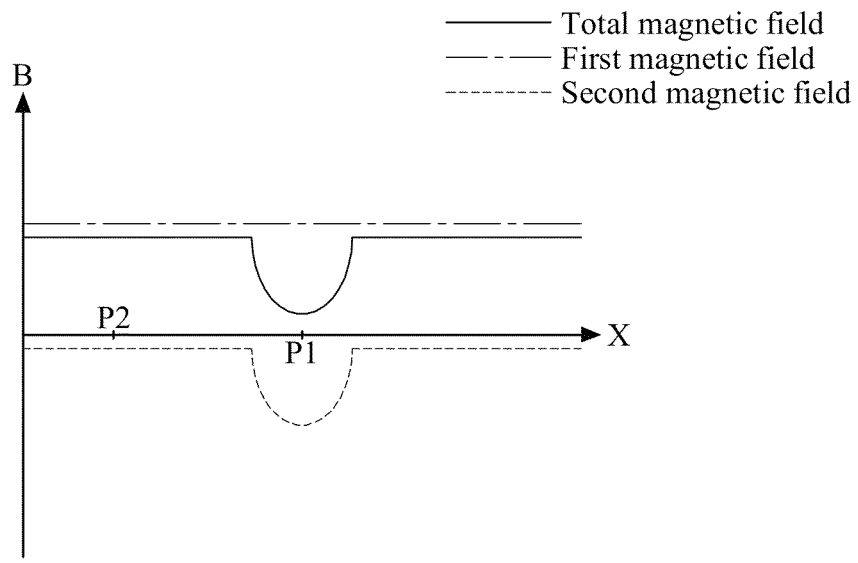
FIG. 5E is a graph of the magnetic field of Step S204 of FIG. 5A.
Figure 5F:
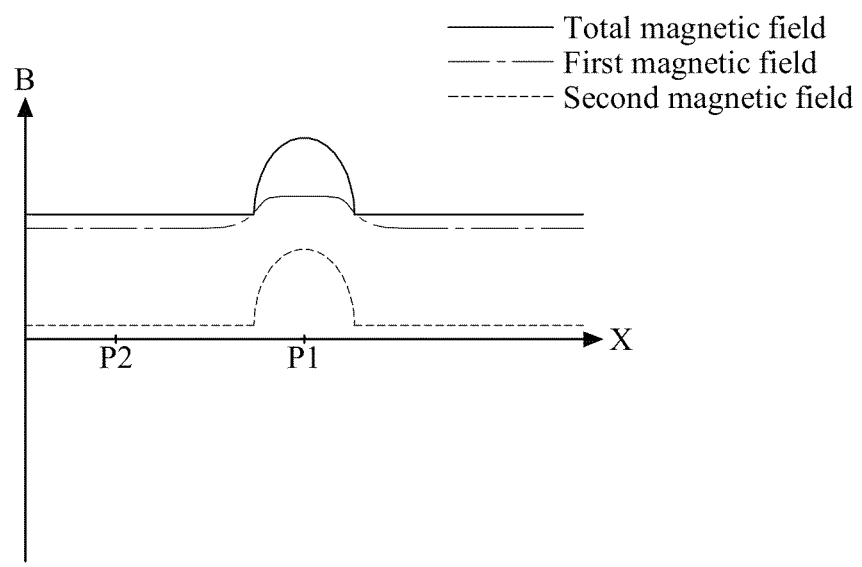
FIG. 5F is another graph of the magnetic field of Step S204 of FIG. 5A.
Figure 5G:
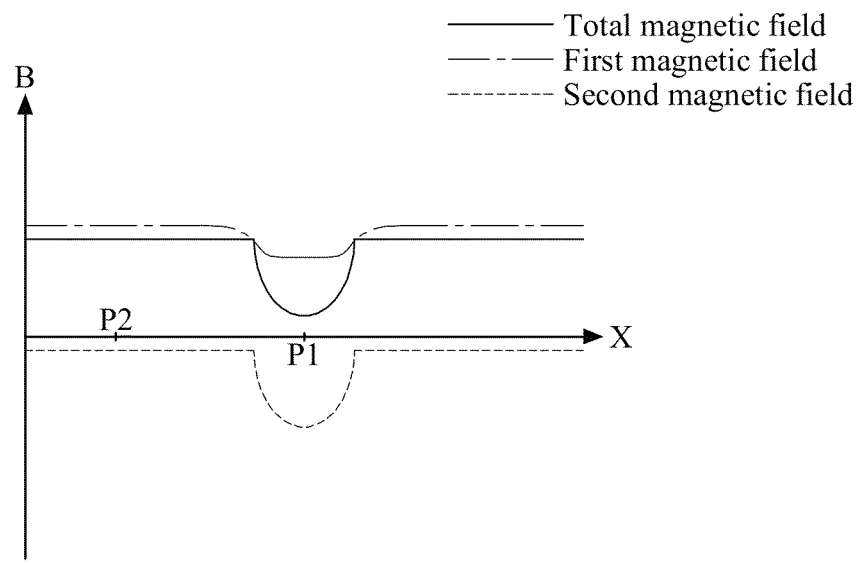
FIG. 5G is another graph of the magnetic field of Step S204 of FIG. 5A.

Next, please refer to FIGS. 1A, 5A-5G. FIG. 5A is a flow chart of a method for manipulating the droplet according to another embodiment of the disclosure, FIG. 5B is a top view of the distribution of the magnetic particle in the droplet of Step S204 of FIG. 5A, FIG. 5C is a top view of the distribution of the magnetic particle in the droplet of Step S204 of FIG. 5A, FIG. 5D is a graph of the magnetic field of Step S204 of FIG. 5A, FIG. 5E is a graph of the magnetic field of Step S204 of FIG. 5A, FIG. 5F is another graph of the magnetic field of Step S204 of FIG. 5A, and FIG. 5G is another graph of the magnetic field of Step S204 of FIG. 5A. The embodiments of FIGS. 5A-5G describe how to control the droplet agitating in the flow channel 11. "Agitating" represents the process of mixing the magnetic particles inside the droplet. In the following descriptions, the droplet is agitated inside one operating space 111, but the disclosure is not limited thereto. In some other embodiments, the user can move and agitate the droplet in the flow channel 11 at the same time. In FIG. 5A, Steps S201 to S203 are the same or similar to Steps S101 to S103 of FIG. 4A, therefore, Steps S201 to S203 are not described again.

After the droplet has the same direction of magnetic field with the first magnetic field, a magnetic force having the same direction to the first magnetic field and a magnetic force having an opposite direction to the first magnetic field are applied on the droplet by the second magnetic field, which is produced by the second magnetic field modules 130, alternatively (S204), so that magnetic particles are agitated in the droplet. Therefore, the magnetic particles and the analytes are fully combined, and the magnetic particles combined with the analytes are mixed in the droplet uniformly by the process of FIG. 5A.

When the magnetic force having the same direction to the first magnetic field is applied on the droplet at the operating space 111 by the second magnetic field modules 130 (as shown in FIGS. 5D and 5F), the magnetic particles M are concentrated in the droplet B by the first magnetic field and the second magnetic field (as shown in FIG. 5B). On the other hand, when the magnetic force having the opposite direction to the first magnetic field is applied on the droplet at the operating space 111 by the second magnetic field modules 130 (as shown in FIGS. 5E and 5G), the magnetic particles M are dispersed in the droplet B (as shown in FIG. 5C).

Furthermore, the user can adjust the intensity of magnetism of the first magnetic field according to the mass of the magnetic particles inside the droplet. When the magnetic particles are too heavy so that the first magnetic field cannot lift the magnetic particles, the magnetic particles are concentrated in the droplet and the dispersion of the magnetic particles is not uniform. Thus, when the magnetic particles in the droplet have a greater weight, a first magnetic field having a greater intensity is produced, so that the dispersion of the magnetic particles in the droplet is more uniform. The magnetic field of the droplet manipulating device 10 in Step S204 is shown in FIGS. 5D-5G. FIGS. 5D and 5E describe the droplets having a lighter weight, and FIGS. 5F and 5G describe the droplets having a greater weight.

Figure 5H:
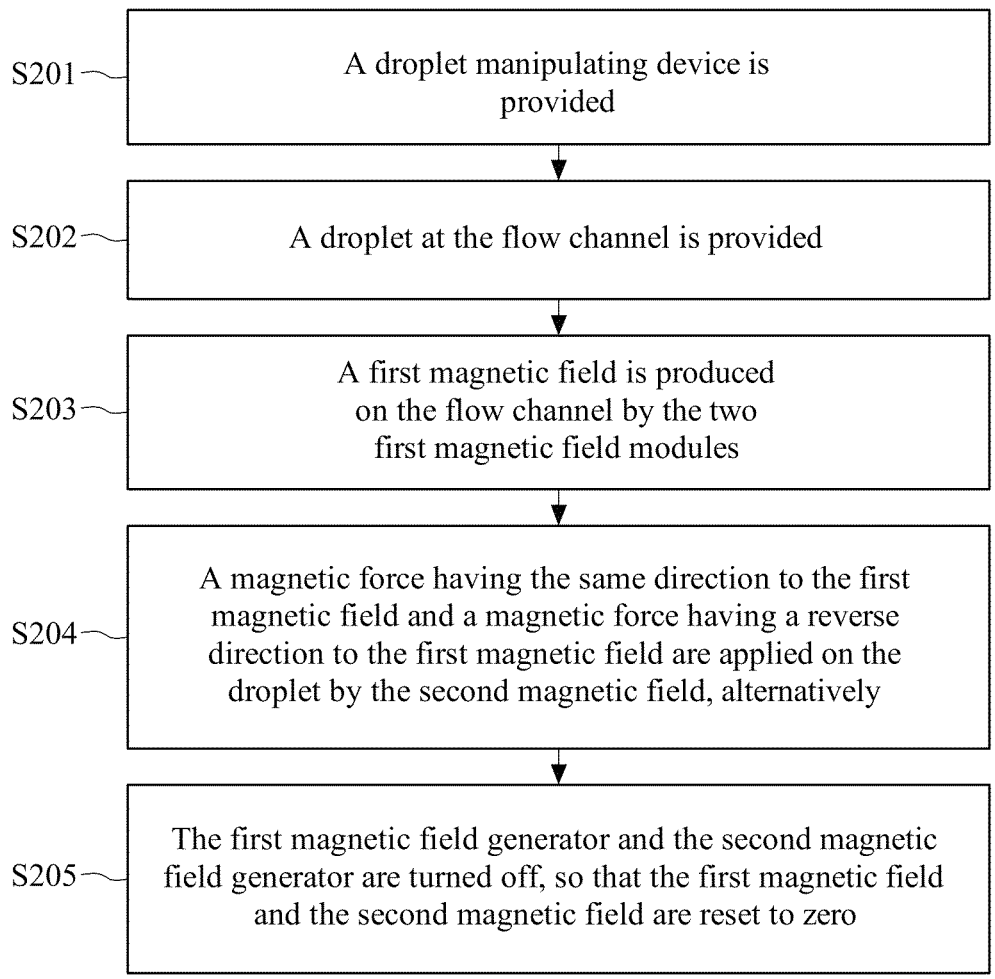
FIG. 5H is a flow chart of a method for manipulating the droplet according to another embodiment of the disclosure.
Figure 5I:
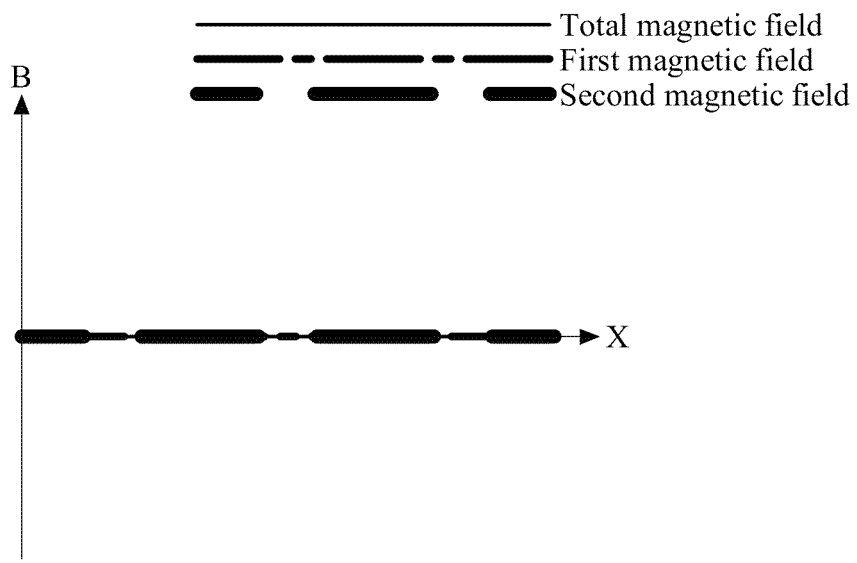
FIG. 5I is a graph of the magnetic field of Step S205 of FIG. 5H.
Figure 5J:
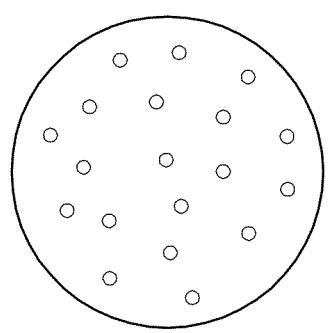
FIG. 5J is a graph of the distribution of the magnetic particle in the droplet of Step S205 of FIG. 5H.

Please refer to FIGS. 5H-5J. FIG. 5H is a flow chart of a method for manipulating the droplet according to another embodiment of the disclosure. FIG. 5I is a graph of the magnetic field of Step S205 of FIG. 5H. FIG. 5J is a graph of the distribution of the magnetic particle in the droplet of Step S205 of FIG. 5H. This embodiment is similar with those in FIG. 5A-5G, so the repeated steps are not described again. In this embodiment, after Step S204, the method further comprises the first magnetic field generator and the second magnetic field generator are turned off, so that the first magnetic field and the second magnetic field are reset to zero (S205). As shown in FIGS. 5I and 5J, the first magnetic field and the second magnetic field are reset to zero, as well as the magnetic particles are uniformly dispersed in the droplet. Therefore, the combination of the magnetic particles and the analytes are improved.

Figure 6A:
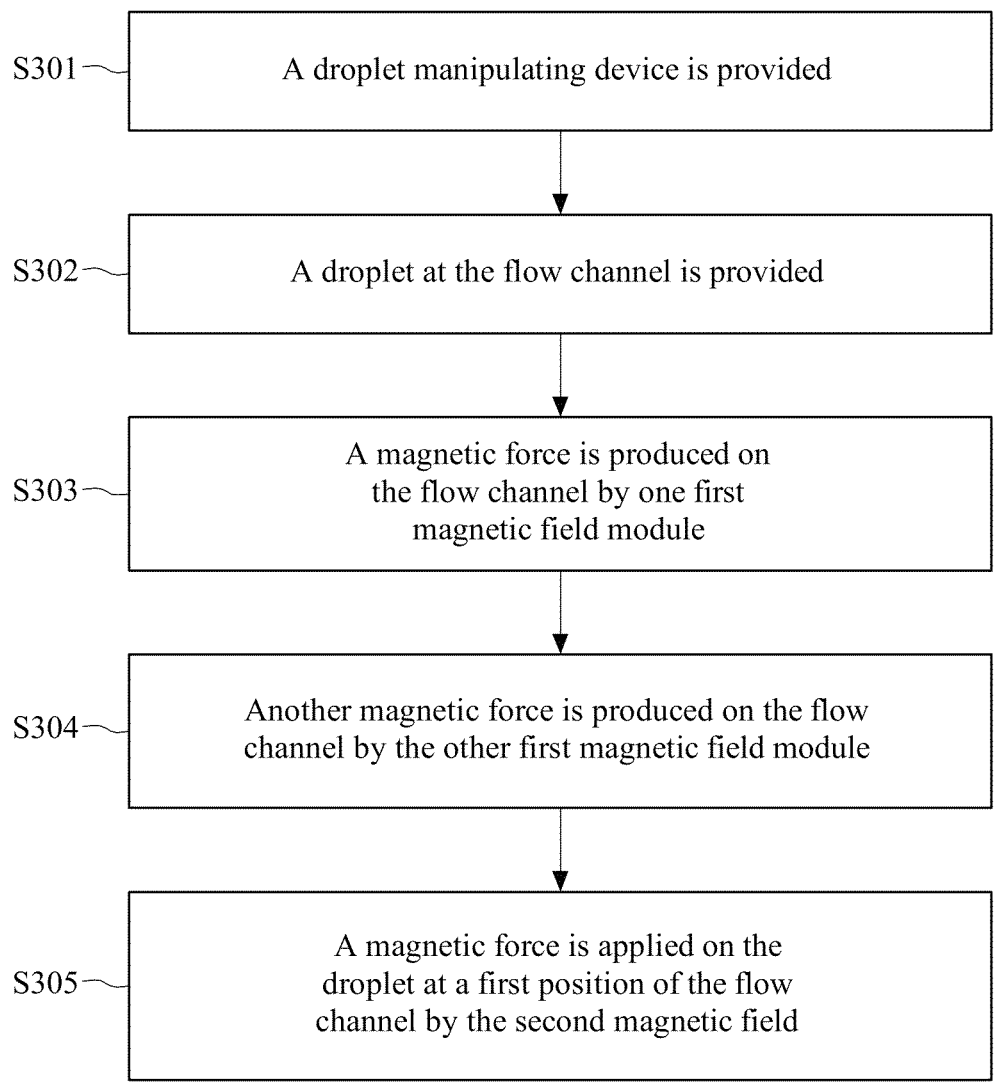
FIG. 6A is a flow chart of a method for manipulating a droplet according to another embodiment of the disclosure.
Figure 6B:
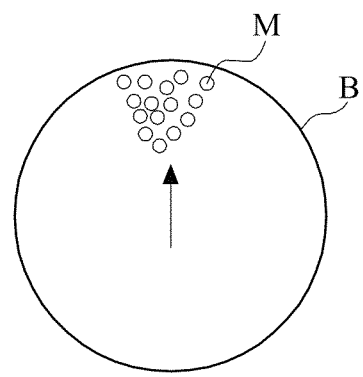
FIG. 6B is a side view of the distribution of the magnetic particle in the droplet of Step S304 of FIG. 6A.
Figure 6C:
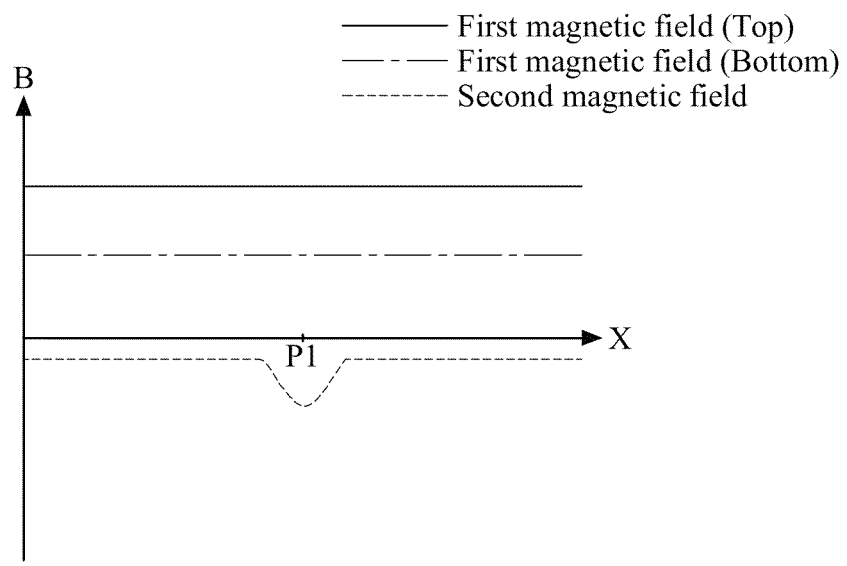
FIG. 6C is a graph of the magnetic field of Step S304 of FIG. 6A.
Figure 6D:
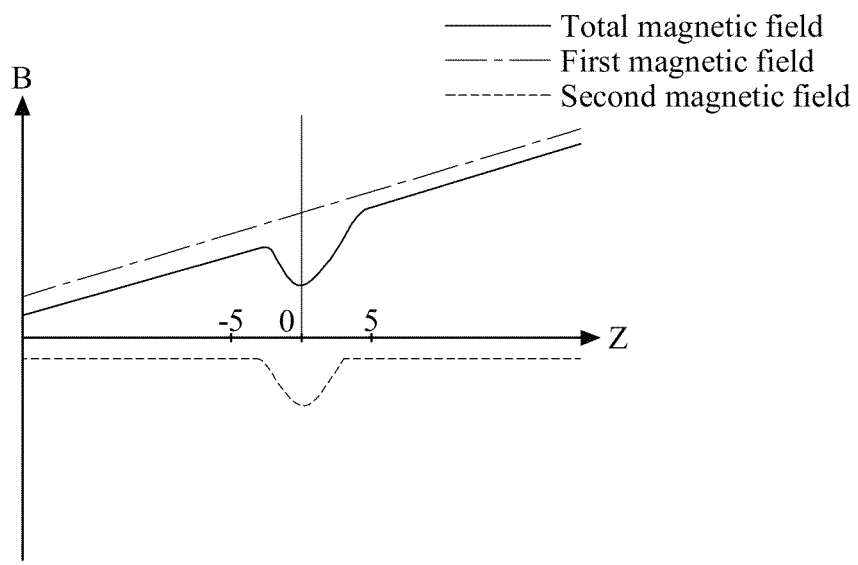
FIG. 6D is another graph of the magnetic field of Step S304 of FIG. 6A.
Figure 6E:
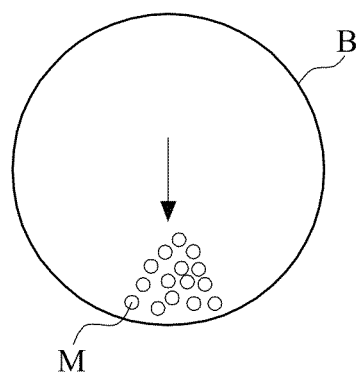
FIG. 6E is another side view of the distribution of the magnetic particle in the droplet of Step S304 of FIG. 6A.
Figure 6F:
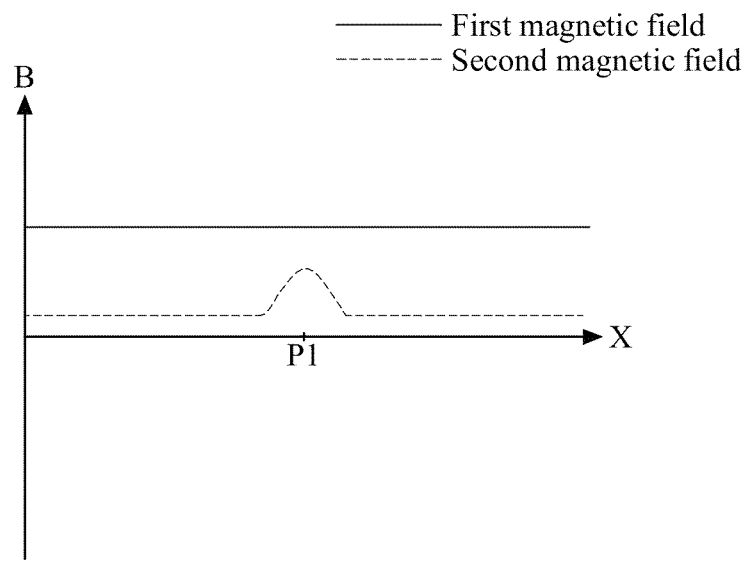
FIG. 6F is another graph of the magnetic field of Step S304 of FIG. 6A.
Figure 6G:
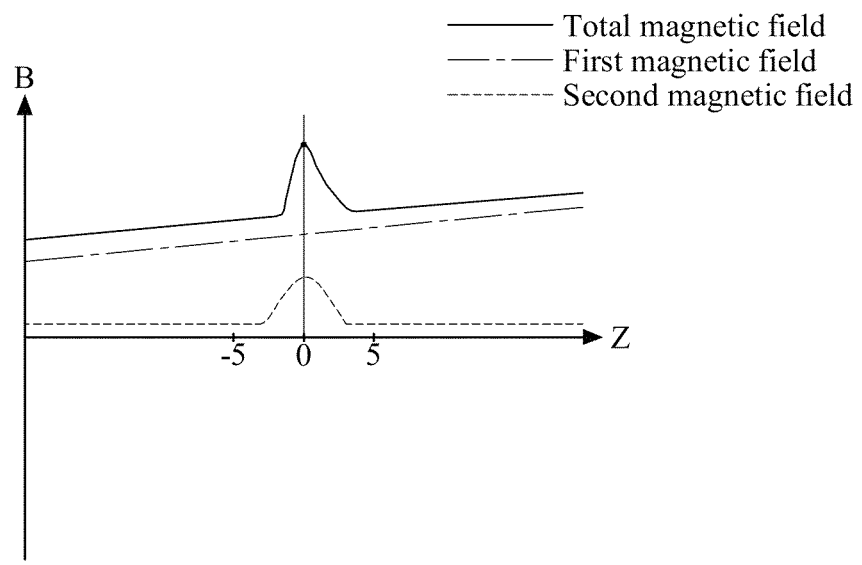
FIG. 6G is another graph of the magnetic field of Step S304 of FIG. 6A.
Figure 6H:
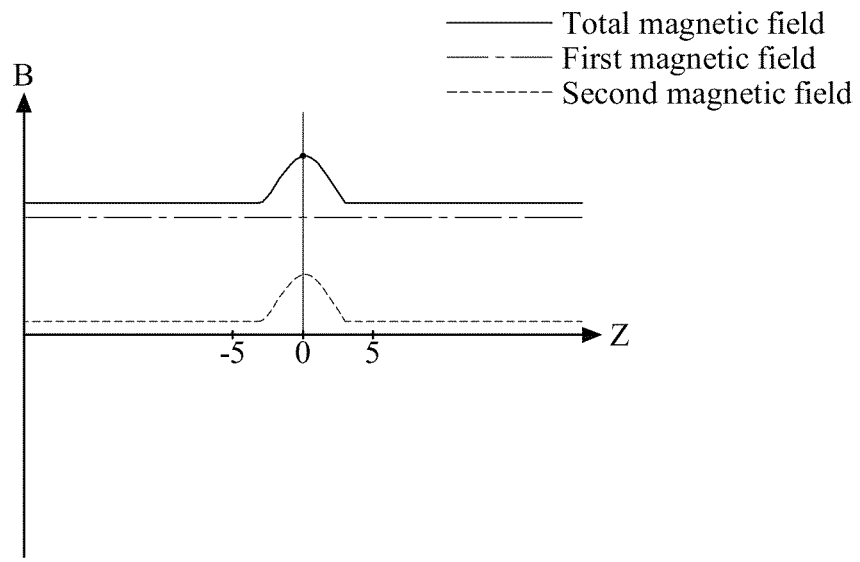
FIG. 6H is another graph of the magnetic field of Step S304 of FIG. 6A.
Figure 6I:
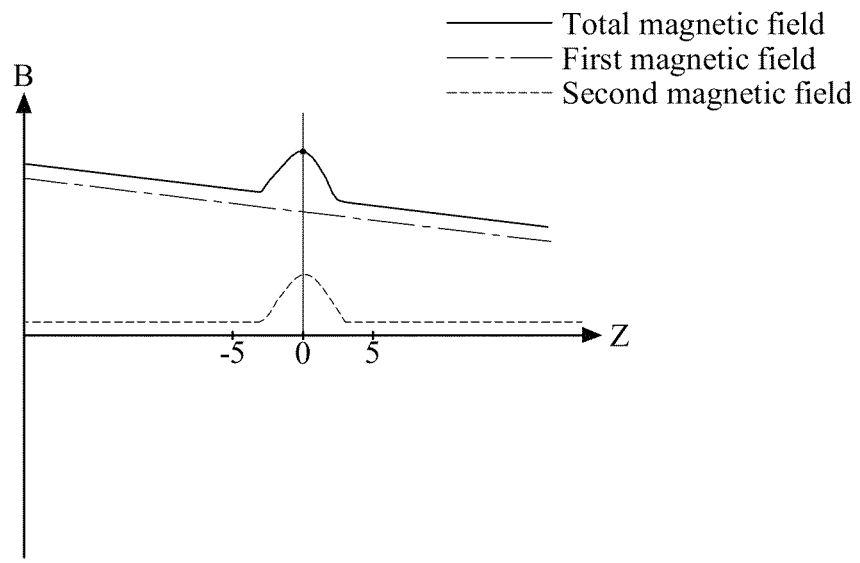
FIG. 6I is another graph of the magnetic field of Step S304 of FIG. 6A.

Next, please refer to FIGS. 1A, and 6A-6I. FIG. 6A is a flow chart of a method for manipulating a droplet according to another embodiment of the disclosure. FIG. 6B is a side view of the distribution of the magnetic particle in the droplet of Step S304 of FIG. 6A. FIG. 6C is a graph of the magnetic field of Step S304 of FIG. 6A. FIG. 6D is another graph of the magnetic field of Step S304 of FIG. 6A. FIG. 6E is another side view of the distribution of the magnetic particle in the droplet of Step S304 of FIG. 6A. FIG. 6F is another graph of the magnetic field of Step S304 of FIG. 6A. FIG. 6G is another graph of the magnetic field of Step S304 of FIG. 6A. FIG. 6H is another graph of the magnetic field of Step S304 of FIG. 6A. FIG. 6I is another graph of the magnetic field of Step S304 of FIG. 6A. In FIG. 6A, Steps S301-S302 are the same or similar to Steps S101-S102 of FIG. 4A as well as Step S305 is the same or similar to Step S104 of FIG. 4A. Therefore, Steps S301-S302 and S305 are not described again.

After a droplet at the flow channel 11 is provided (S302), a magnetic force is produced on the flow channel by one first magnetic field module (top) (S303). Then, another magnetic force is produced on the flow channel by the other first magnetic field module (bottom) (S304). In this and some other embodiments, the magnetic forces have the same directions (which are opposite to the direction of the second magnetic field) and the intensities of magnetism of the magnetic forces are different. Then, a magnetic force is applied on the droplet at a first position of the flow channel by the second magnetic field S(305). In FIGS. 6B-6D, the directions of the magnetic forces produced by the first magnetic field modules are opposite to the direction of the magnetic force produced by the second magnetic field, and the intensity of magnetism of the magnetic forces produced by the first magnetic field module (top) is greater than the intensity of magnetism of the magnetic forces produced by the first magnetic field module (bottom). FIG. 6D shows the variation of the intensity of magnetism of the magnetic force along the z-axis. As shown in FIG. 6D, the intensity of magnetism of the magnetic force at the surface of the flow channel (z=0, the bottom region in the droplet) is smaller than the intensity of magnetism of the magnetic force at the top region in the droplet. Therefore, the magnetic particles in the droplet move toward the top region in the droplet (as shown in FIG. 6B). As shown in FIGS. 6E-6I, the directions of the magnetic forces produced by the first magnetic field modules are the same with the direction of the magnetic force produced by the second magnetic field. In this and some other embodiments, the intensity of magnetism of the magnetic forces produced by the first magnetic field module (top) can be greater than the intensity of magnetism of the magnetic forces produced by the first magnetic field module (bottom) (as shown in FIG. 6G). In some other embodiments, the intensity of magnetism of the magnetic forces produced by the first magnetic field module (top) can be equal to the intensity of magnetism of the magnetic forces produced by the first magnetic field module (bottom) (as shown in FIG. 6H). In some other embodiments, the intensity of magnetism of the magnetic forces produced by the first magnetic field module (top) can be less than the intensity of magnetism of the magnetic forces produced by the first magnetic field module (bottom) (as shown in FIG. 6I). Regarding the above embodiments, the magnetic forces produced by the first magnetic field modules have the same directions (which are the same as the direction of the second magnetic field). The intensity of magnetism of the magnetic force at the surface of the flow channel (z=0, the bottom region in the droplet) is greater than the intensity of magnetism of the magnetic force at other places (as shown in FIG. 6G-6I). Therefore, the magnetic particles in the droplet move toward the bottom region in the droplet. By the process of Steps S301-S305, the magnetic particles in the droplet are capable of moving in different regions in the droplet, so that the magnetic particles and the analytes are fully combined, and the magnetic particles combined with the analytes are mixed in the droplet uniformly by the process of FIG. 6A.

Figure 7A:
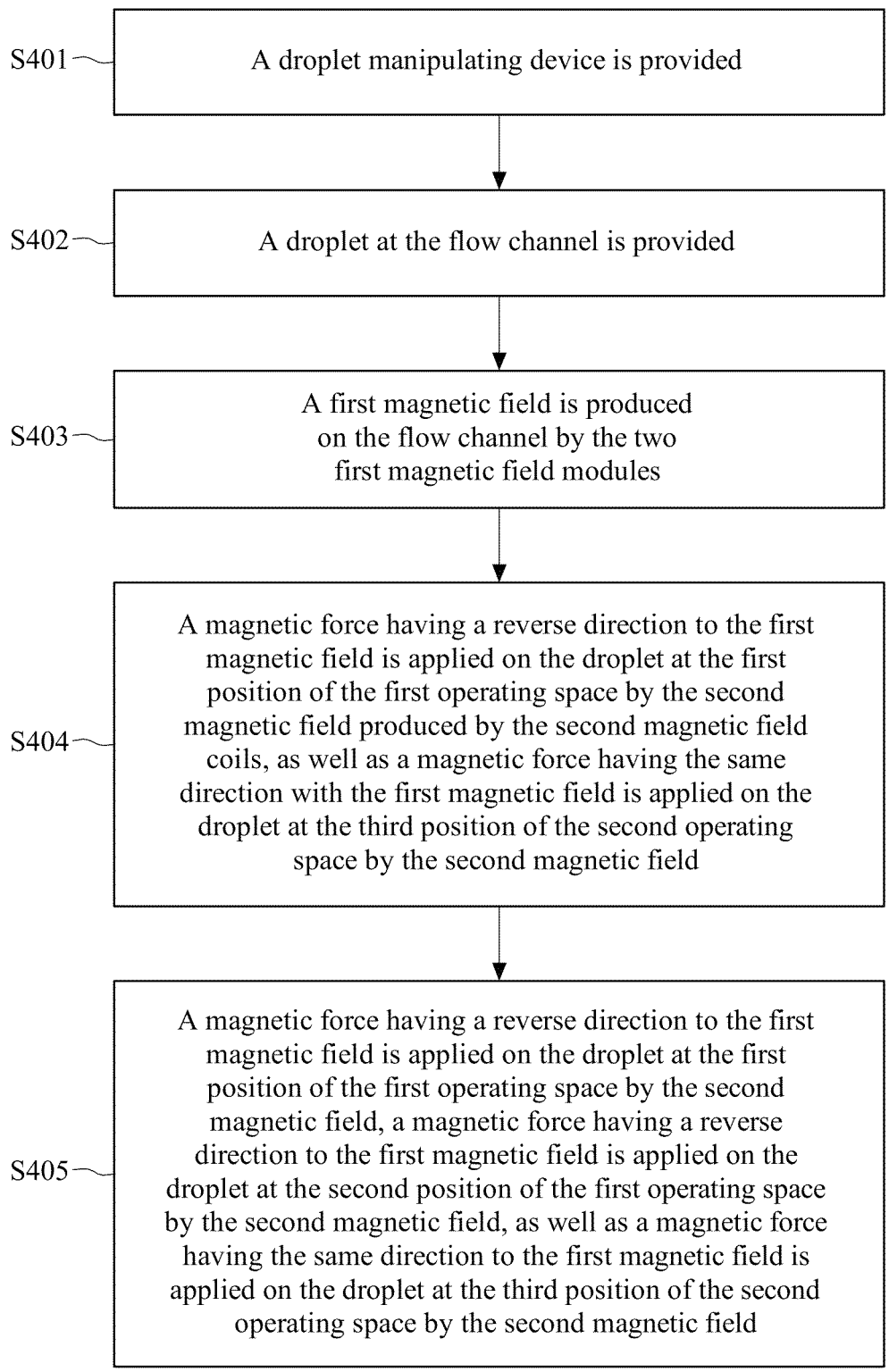
FIG. 7A is a flow chart of a method for manipulating a droplet according to another embodiment of the disclosure.
Figure 7B:
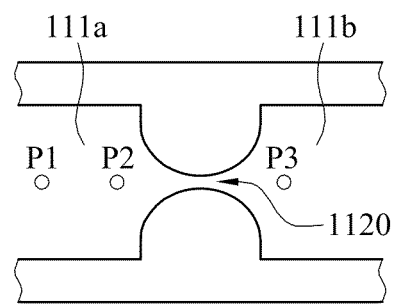
FIG. 7B is a top view of the flow channel of the droplet manipulating device of FIG. 7A.
Figure 7C:
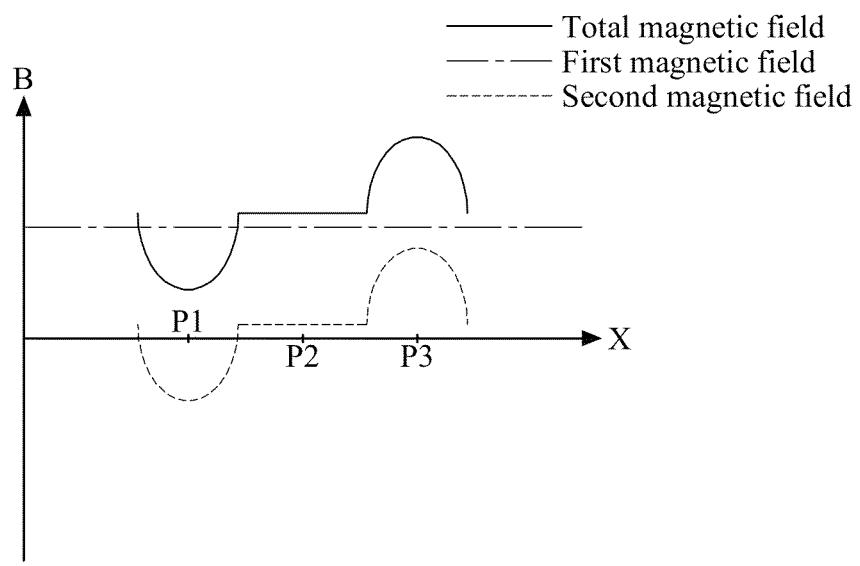
FIG. 7C is a graph of the magnetic field of Step S404 of FIG. 7A.
Figure 7D:
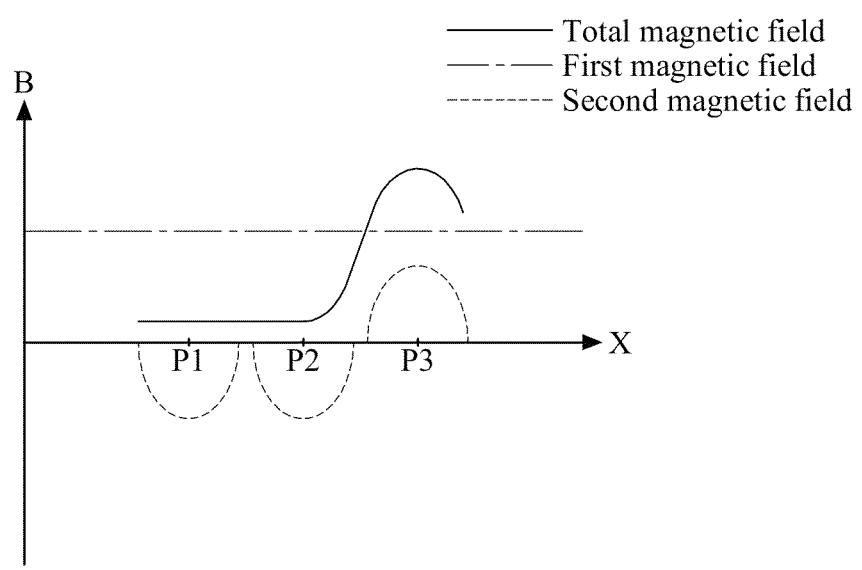
FIG. 7D is a graph of the magnetic field of Step S405 of FIG. 7A.

Next, please refer to FIGS. 1A, and 7A-7D. FIG. 7A is a flow chart of a method for manipulating a droplet according to another embodiment of the disclosure, FIG. 7B is a top view of the flow channel of the droplet manipulating device of FIG. 7A, FIG. 7C is a graph of the magnetic field of Step S404 of FIG. 7A, and FIG. 7D is a graph of the magnetic field of Step S405 of FIG. 7A. The embodiments of FIGS. 7A-7D describe how to control the movement of the droplet in the flow channel 11. The droplet moving from a first operating space 111a and concentrating at the gap 1120 of the separating unit 112 is described herein. In FIG. 7A, steps S401 to S403 are the same or similar to Steps S101 to S103 of FIG. 4A, therefore, Steps S401 to S403 are not described again.

After the droplet has the same direction of magnetic field with the first magnetic field, at a first time point, a magnetic force having an opposite direction to the first magnetic field is applied on the droplet at the first position P1 of the first operating space 111a by the second magnetic field produced by the second magnetic field coils 130, as well as a magnetic force having the same direction with the first magnetic field is applied on the droplet at the third position P3 of the second operating space 111b by the second magnetic field (S404). Then, at a second time point after the first time point, a magnetic force having an opposite direction to the first magnetic field is applied on the droplet at the first position P1 of the first operating space 111a by the second magnetic field, a magnetic force having an opposite direction to the first magnetic field is applied on the droplet at the second position P2 of the first operating space 111a by the second magnetic field, as well as a magnetic force having the same direction to the first magnetic field is applied on the droplet at the third position P3 of the second operating space 111b by the second magnetic field (S405). The second position P2 is closer to the second operating space 111b than the first position P1. Therefore, the droplet moves from the first operating space 111a and concentrates at the gap 1120, which is adjacent to the first operating space 111a, by the variation of the second magnetic field at the flow channel 11 with time. The magnetic field produced by the droplet manipulating device 10 in Step S404 is shown in FIG. 7C, and the magnetic field produced by the droplet manipulating device 10 in Step S405 is shown in FIG. 7D.

Figure 7E:
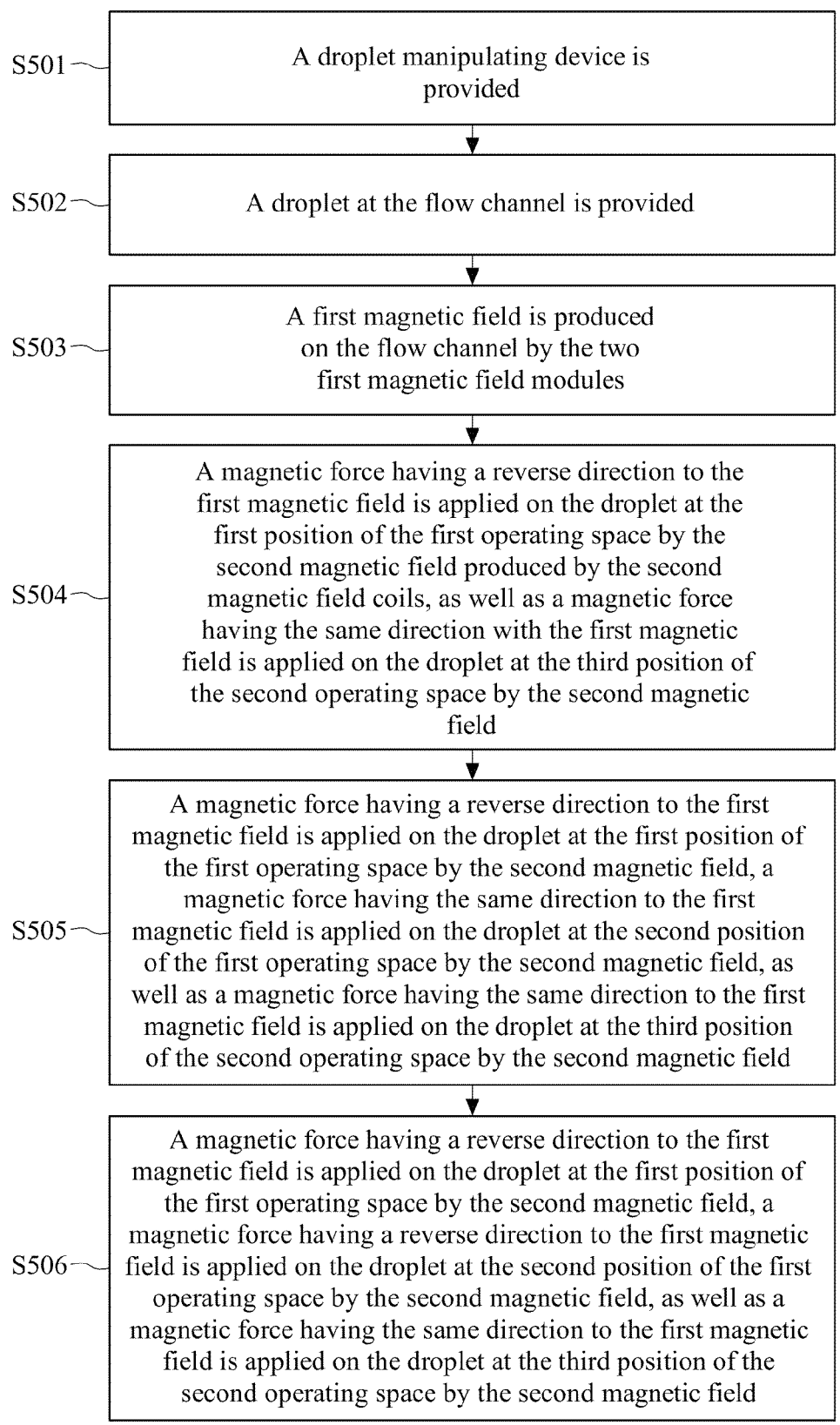
FIG. 7E is a flow chart of a method for manipulating a droplet according to another embodiment of the disclosure.
Figure 7F:
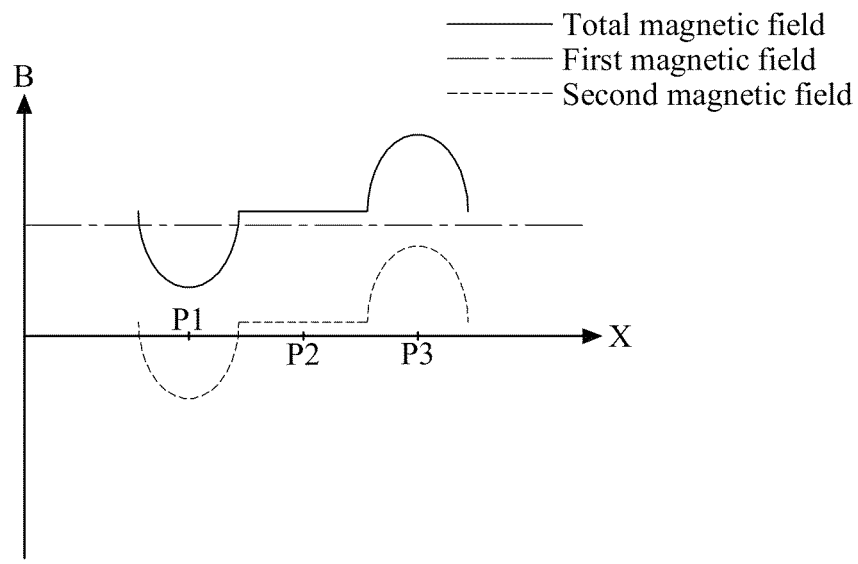
FIG. 7F is a graph of the magnetic field of Step S504 of FIG. 7E.
Figure 7G:
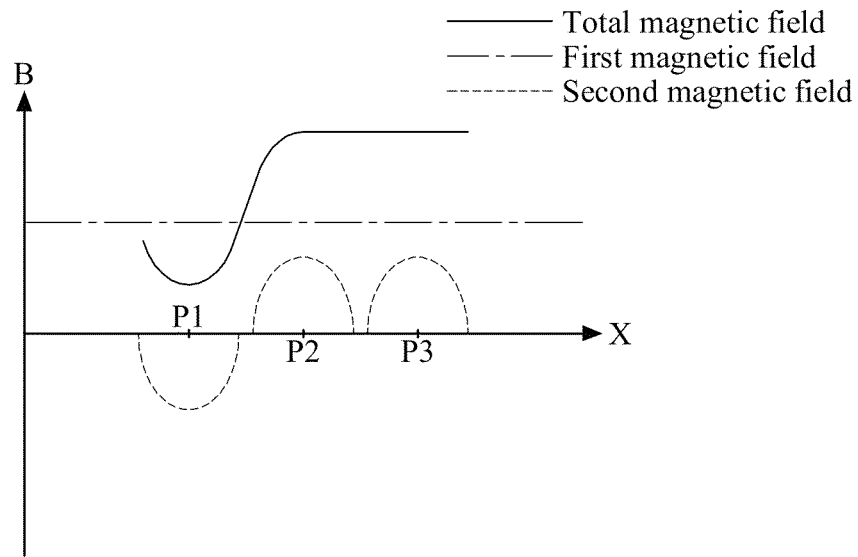
FIG. 7G is a graph of the magnetic field of Step S505 of FIG. 7E.
Figure 7H:
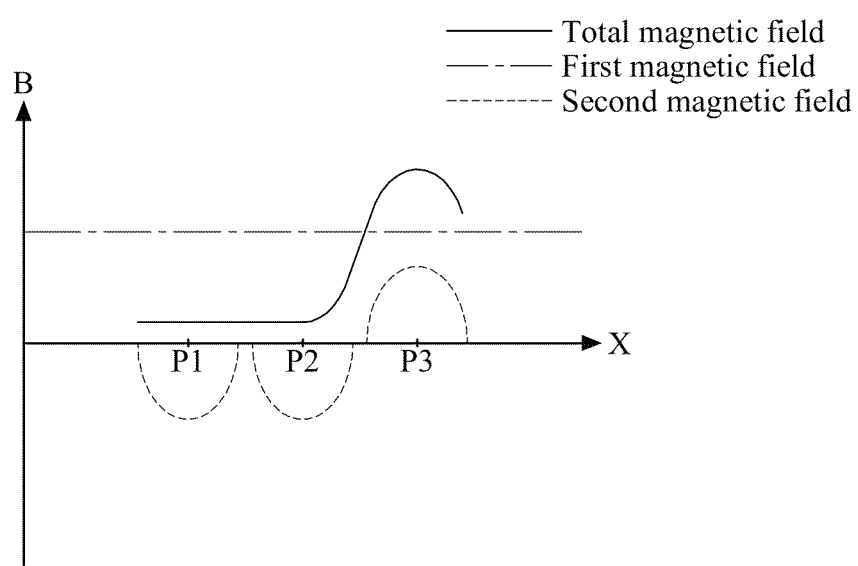
FIG. 7H is a graph of the magnetic field of Step S506 of FIG. 7E.

Next, please refer to FIGS. 1A, 6B, and 7E-7H, FIG. 7E is a flow chart of a method for manipulating a droplet according to another embodiment of the disclosure, FIG. 7F is a graph of the magnetic field of Step S504 of FIG. 7E, FIG. 7G is a graph of the magnetic field of Step S505 of FIG. 7E, and FIG. 7H is a graph of the magnetic field of Step S506 of FIG. 7E. The embodiments of FIGS. 7E-7G are similar to the embodiments of FIGS. 7A, 7C, and 7D. The differences are that the embodiments of FIG. 7E further comprise an operating process at a third time point between the first time point and the second time point of the embodiments of FIG. 7A.

At the third time point, which is between the first time point and the second time point, a magnetic force having an opposite direction to the first magnetic field is applied on the droplet at the first position P1 of the first operating space $111a$ by the second magnetic field, a magnetic force having the same direction to the first magnetic field is applied on the droplet at the second position P2 of the first operating space $111a$ by the second magnetic field, as well as a magnetic force having the same direction to the first magnetic field is applied on the droplet at the third position P3 of the second operating space $111b$ by the second magnetic field (S505). The second position P2 is closer to the second operating space $111b$ than the first position P1. Therefore, the droplet is more concentrated at the gap 1120 by Step S505 before the droplet moves to the second operating space $111b$. Also, magnetic particles remaining in the first operating space $111a$ when other magnetic particles move to the second operating space $111b$ by Step S506 can be avoided by performing Step S505. The magnetic field produced by the droplet manipulating device 10 in Step S504 is shown in FIG. 7F, the magnetic field produced by the droplet manipulating device 10 in Step S505 is shown in FIG. 7G, as well as the magnetic field produced by the droplet manipulating device 10 in Step S506 is shown in FIG. 7H.

Figure 8A:
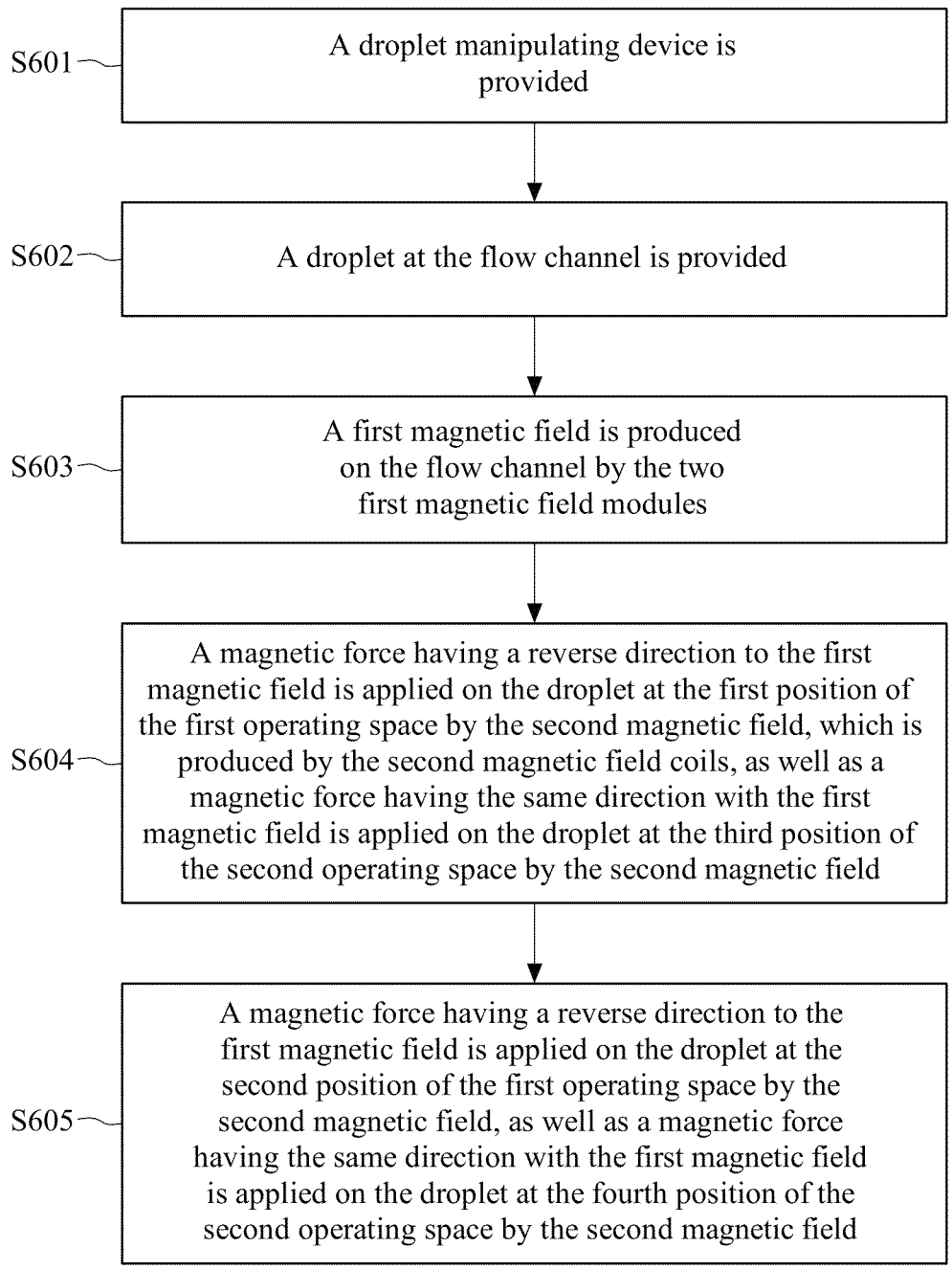
FIG. 8A is a flow chart of a method for manipulating a droplet according to another embodiment of the disclosure.
Figure 8B:
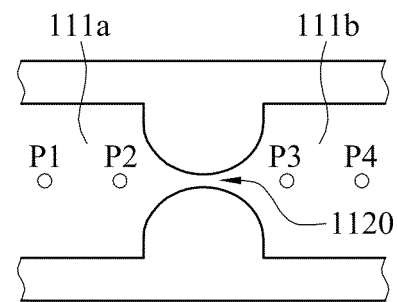
FIG. 8B is a top view of the flow channel of the droplet manipulating device of FIG. 8A.
Figure 8C:
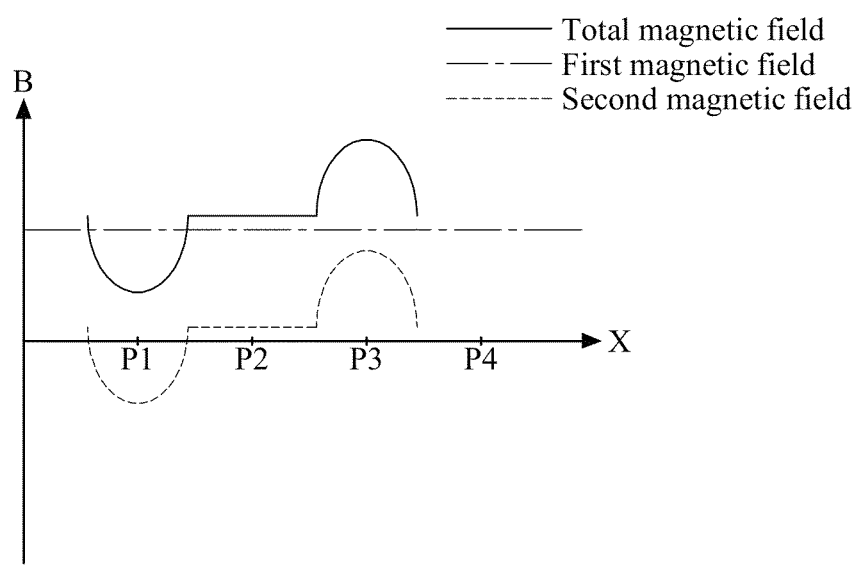
FIG. 8C is a graph of the magnetic field of Step S604 of FIG. 8A.
Figure 8D:
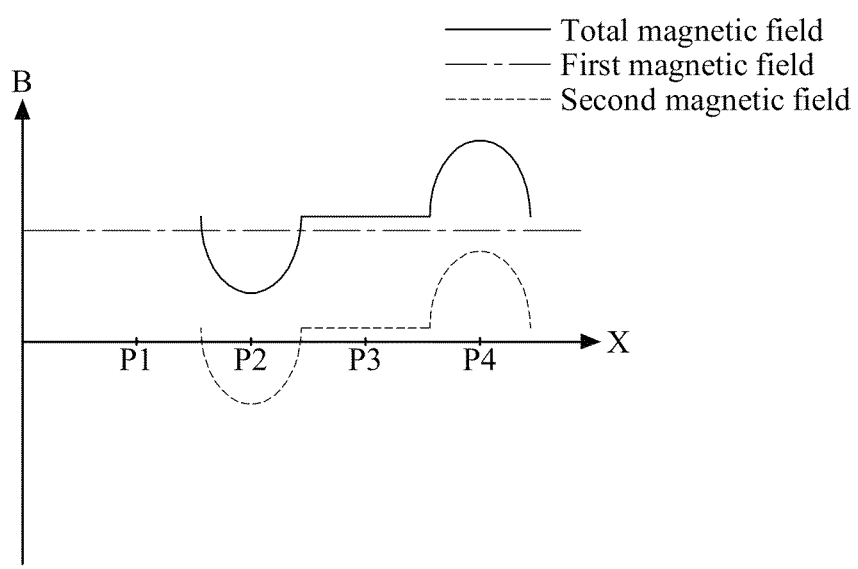
FIG. 8D is a graph of the magnetic field of Step S605 of FIG. 8A.

Please refer to FIGS. 1A, and 8A-8D. FIG. 8A is a flow chart of a method for manipulating a droplet according to another embodiment of the disclosure, FIG. 8B is a top view of the flow channel of the droplet manipulating device of FIG. 8A, FIG. 8C is a graph of the magnetic field of Step S604 of FIG. 8A, and FIG. 8D is a graph of the magnetic field of Step S605 of FIG. 8A. The embodiments of FIGS. 8A-8D describe how to control the movement of the droplet in the flow channel 11. This embodiment describes the droplet moving from the gap 1120 to a second operating space $111b$ that is adjacent to the gap 1120. Moreover, the user may adapt the embodiment in FIGS. 7A, and 8A-8D together in sequence to move the magnetic particles from a first operating space $111a$ to the gap 1120, and to move the magnetic particles from the gap 1120 to a second operating space $111b$. Therefore, the magnetic particles in the droplet moves between the operating spaces $111a$ and $111b$ in the flow channel 11. In FIG. 8A, Steps S601 to S603 are the same or similar to Steps S101 to S103 of FIG. 4A, therefore, Steps S601 to S603 are not described again.

After the droplet has the same direction of magnetic field with the first magnetic field, at a first time point, a magnetic force having an opposite direction to the first magnetic field is applied on the droplet at the first position P1 of the first operating space $111a$ by the second magnetic field, which is produced by the second magnetic field coils 130, as well as a magnetic force having the same direction with the first magnetic field is applied on the droplet at the third position P3 of the second operating space $111b$ by the second magnetic field (S604). Then, at a second time point after the first time point, a magnetic force having an opposite direction to the first magnetic field is applied on the droplet at the second position P2 of the first operating space $111a$ by the second magnetic field, as well as a magnetic force having the same direction with the first magnetic field is applied on the droplet at the fourth position P4 of the second operating space $111b$ by the second magnetic field (S605). The second position P2 is closer to the second operating space $111b$ than the first position P1, and the third position P3 is closer to the first operating space $111a$ than the fourth position P4. Therefore, the droplet moves from the gap 1120 to the second operating space $111b$ adjacent to the gap 1120 by the variation of the second magnetic field at the flow channel 11. The magnetic field produced by the droplet manipulating device 10 at Step S604 is shown in FIG. 8C, and the magnetic field produced by the droplet manipulating device 10 at Step S605 is shown in FIG. 8D.

According to the embodiments of FIGS. 4A, 5A, 6A, 7A and 8A, the user can accomplish detections by adapting the above embodiments together. For instance, the user places an analyte in a first operating space. Then, the user mixes the analyte and the droplet by the embodiment of FIG. 4A. Then, the user mixes the analyte and the droplet more completely so that the analyte and the droplet are combined more completely by the embodiments of FIGS. 5A and/or 6A. Then, the droplet concentrates in the gap by the embodiment of FIG. 7A. Then, the droplet moves from the gap to another operating space by the embodiment of FIG. 8A. In the other operating space, an analyzing liquid is provided so as to detect the analyte, which is combined with the magnetic particle. After the detection, the magnetic particles in the droplet move to another operating space by the embodiments of FIGS. 7A and 8A. In some other examples, the analyte combines with the magnetic particle by the embodiments of FIGS. 4A, 5A and 6A, the magnetic particles in the droplet move to another operating space by the embodiments of FIGS. 7A and 8A, as well as the analyte is cleaned by the embodiments of FIGS. 4A and 5A. According to the above descriptions, the embodiments of FIGS. 4A, 5A, 6A, 7A and 8A may be combined according to the user's need.

Figure 9:
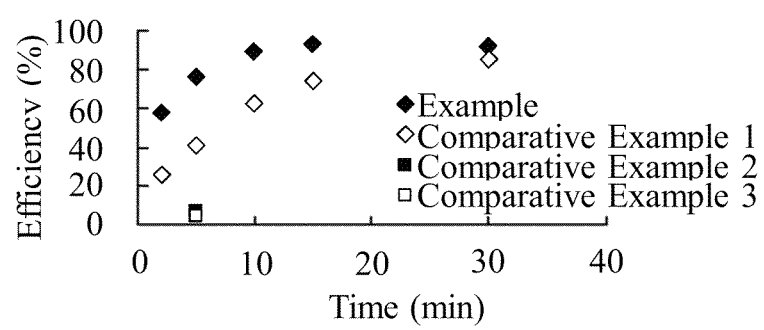
FIG. 9 is a graph of the binding efficiencies and the mixing time.

Please refer to FIG. 9, which is a graph of the binding efficiencies and the mixing time. Example represents the binding efficiencies between the magnetic particles in the droplet and the analytes when the droplet is mixed with the analytes by the droplet manipulating device of the embodiments. Comparative example 1 represents the binding efficiencies between the magnetic particles in the droplet and the analytes when the droplet is mixed with the analytes by an ELISA plate-based assay. Comparative Example 2 represents the binding efficiency between the magnetic particles in the droplet and the analytes before the droplet is mixed with the analytes by the droplet manipulating device of the embodiments. Comparative Example 3 represents the binding efficiency between the magnetic particles in the droplet and the analytes before the droplet is mixed with the analytes by an ELISA plate-based assay.

Before mixing the magnetic particles and the analytes, the binding efficiencies between the magnetic particles and the analytes are about zero (Comparative Example 2 and Comparative Example 3). When the droplet is mixed with the analytes, the binding efficiencies between the magnetic particles and the analytes mixed by the droplet manipulating device of the embodiments are greater than the binding efficiencies between the magnetic particles and the analytes mixed by an ELISA plate-based assay. Therefore, the droplet manipulating device and the method for manipulating a droplet are more rapid and more sufficient to mix the magnetic particles and the analytes.

According to the droplet manipulating device and the method for manipulating a droplet of the disclosure, the droplet has the direction of magnetic field corresponding to the first magnetic field by the first magnetic field generator. Then, the droplet is in motion according to the second magnetic field, which is produced by the second magnetic field generator. Since the motion of the droplet is controlled by the interaction of the two magnetic fields, the magnetic field is more uniform.

In addition, the droplet can be transported, mixed, separated, agitated, or cut by the first magnetic field and the variation of the second magnetic field. Therefore, transport, mix, separation, agitation, or cut of the droplet can be manipulated, and motions of multiple droplets can be manipulated.

In addition, each of the procedures (e.g. pre-treatment, detection, or post-treatment) can be accomplished in the same droplet manipulating device. Therefore, the whole process can be regarded as a method of lab-on-chip and it is more convenient.

In some other embodiments, the first magnetic field modules are disposed on the rails, and the first magnetic field modules move according to the position of the droplet. Therefore, the first magnetic field is only produced at the position of the droplet. Thus, the first magnetic field modules and the produced first magnetic field do not need to cover the whole droplet manipulating device. Accordingly, the first magnetic field modules can have a smaller size, and the first magnetic field modules only need less power to operate.

What is claimed is:

1. A droplet manipulating device, comprising:
   a flow channel adapted for accommodating a droplet;
   a first magnetic field generator comprising two first magnetic field modules opposite to each other, wherein the two first magnetic field modules are at two opposite sides of the flow channel, respectively, for producing a first magnetic field on the flow channel; and
   a second magnetic field generator disposed between the two first magnetic field modules, wherein the second magnetic field generator comprises a plurality of second magnetic field coils for producing a second magnetic field on the flow channel;
   wherein, the droplet driven by the first magnetic field and the second magnetic field is in motion in the flow channel.

2. The droplet manipulating device according to claim 1, wherein each of the first magnetic field modules has at least one first magnetic field coil.

3. The droplet manipulating device according to claim 1, further comprising:
   a first rail module, comprising two rails disposed at the two opposite sides of the flow channel, respectively, and the two first magnetic field modules are movably disposed on the two rails.

4. The droplet manipulating device according to claim 1, further comprising:
   a second rail module comprising at least one rail, wherein the flow channel and the second magnetic field generator are movably disposed on the at least one rail.

5. The droplet manipulating device according to claim 1, further comprising:
   a power controller electrically connected to the first magnetic field generator and the second magnetic field generator for controlling an intensity of magnetism of the first magnetic field and an intensity of magnetism of the second magnetic field.

6. The droplet manipulating device according to claim 1, wherein the flow channel comprises a plurality of operating spaces and at least one separating unit, the separating unit is disposed between the two operating spaces adjacent to each other, the at least one separating unit has a gap, the two operating spaces are connected with each other through the gap, and wherein at least one magnetic particle in the droplet, driven by the first magnetic field and the second magnetic field, moves from one of the operating spaces to another one of the operating spaces through the gap.

7. The droplet manipulating device according to claim 6, wherein the separating unit is located between two of the second magnetic field coils adjacent to each other.

8. The droplet manipulating device according to claim 6, wherein the cross sectional area of each of the operating spaces is greater than the cross sectional area of the gap of the separating unit.

9. The droplet manipulating device according to claim 1, wherein an inner surface of the flow channel is a hydrophobic surface.

10. The droplet manipulating device according to claim 6, wherein each of the operating spaces corresponds to at least two of the second magnetic field coils.

11. The droplet manipulating device according to claim 1, wherein the plurality of second magnetic field coils are disposed between the two first magnetic field modules and are arranged in an array.

* * * * *